(12) United States Patent
Rubin et al.

(10) Patent No.: US 12,192,284 B2
(45) Date of Patent: Jan. 7, 2025

(54) COMMUNICATION SYSTEM AND METHOD

(71) Applicant: Microsoft Technology Licensing, LLC, Redmond, WA (US)

(72) Inventors: David Rubin, Stamford, CT (US); George N. Kustas, Poughkeepsie, NY (US); Michael T. Trombly, Burlington, VT (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 349 days.

(21) Appl. No.: 17/518,431

(22) Filed: Nov. 3, 2021

(65) Prior Publication Data

US 2022/0137921 A1 May 5, 2022

Related U.S. Application Data

(60) Provisional application No. 63/129,301, filed on Dec. 22, 2020, provisional application No. 63/113,439,
(Continued)

(51) Int. Cl.
*H04L 67/12* (2022.01)
*G06F 3/16* (2006.01)
(Continued)

(52) U.S. Cl.
CPC .............. *H04L 67/12* (2013.01); *G06F 3/167* (2013.01); *G06F 16/258* (2019.01);
(Continued)

(58) Field of Classification Search
USPC ...................................................... 704/1–504
See application file for complete search history.

(56) References Cited

U.S. PATENT DOCUMENTS 7,254,782 B1 8/2007 Sherer
7,835,560 B2 11/2010 Vining et al.
(Continued)

FOREIGN PATENT DOCUMENTS

CA 2715825 A1 8/2009
CN 112101552 A 12/2020
(Continued)

OTHER PUBLICATIONS

"Advisory Action Issued in U.S. Appl. No. 17/518,451", Mailed Date: Apr. 20, 2023, 5 Pages.
(Continued)

*Primary Examiner* — Marcus T Riley
(74) *Attorney, Agent, or Firm* — Brian J. Colandreo; Heath M. Sargeant; Holland & Knight LLP

(57) ABSTRACT

A method, computer program product, and computing system for defining a communication computing system within a computing network, wherein the computing network includes a plurality of disparate platforms configured to provide information concerning various topics; enabling a user to issue a verbal command concerning one or more of the plurality of disparate platforms; processing the verbal command to generate a platform-useable command based, at least in part, upon the verbal command; and providing the platform-useable command to at least a portion of the plurality of disparate platforms via the communication computing system.

24 Claims, 11 Drawing Sheets

Related U.S. Application Data filed on Nov. 13, 2020, provisional application No. 63/109,219, filed on Nov. 3, 2020.

(51) Int. Cl.
| | |
|---|---|
| *G06F 16/25* | (2019.01) |
| *G06F 40/174* | (2020.01) |
| *G06F 40/186* | (2020.01) |
| *G10L 15/22* | (2006.01) |
| *G16H 10/40* | (2018.01) |
| *G16H 10/60* | (2018.01) |
| *G16H 15/00* | (2018.01) |
| *G16H 30/00* | (2018.01) |
| *G16H 30/20* | (2018.01) |
| *G16H 30/40* | (2018.01) |
| *G16H 50/20* | (2018.01) |
| *G16H 80/00* | (2018.01) |
| *H04L 67/51* | (2022.01) |

(52) U.S. Cl.
CPC .......... *G06F 40/174* (2020.01); *G06F 40/186* (2020.01); *G10L 15/22* (2013.01); *G16H 10/60* (2018.01); *G16H 15/00* (2018.01); *G16H 30/00* (2018.01); *G16H 30/20* (2018.01); *G16H 80/00* (2018.01); *H04L 67/51* (2022.05); *G10L 2015/223* (2013.01); *G16H 10/40* (2018.01); *G16H 30/40* (2018.01); *G16H 50/20* (2018.01)

(56) References Cited

U.S. PATENT DOCUMENTS

| | | | |
|---|---|---|---|
| 8,601,018 | B2 | 12/2013 | Six et al. |
| 8,712,772 | B2 | 4/2014 | Oez |
| 8,850,304 | B2 | 9/2014 | Ye |
| 9,112,863 | B2 | 8/2015 | Gnech et al. |
| 10,332,639 | B2 | 6/2019 | Smurro |
| 10,360,675 | B2 | 7/2019 | Reicher et al. |
| 10,447,610 | B1 | 10/2019 | Shah et al. |
| 10,510,449 | B1 | 12/2019 | Reicher et al. |
| 10,614,111 | B2 | 4/2020 | Moeller-bertram et al. |
| 10,614,196 | B2 | 4/2020 | Maitra |
| 10,719,301 | B1 | 7/2020 | Dasgupta et al. |
| 10,860,741 | B1 | 12/2020 | Liu |
| 10,909,129 | B2 | 2/2021 | Sevenster |
| 11,183,302 | B1 | 11/2021 | McNair |
| 11,357,582 | B1 | 6/2022 | Roh |
| 11,442,534 | B1* | 9/2022 | Douglas ............... G06F 3/0346 |
| 11,461,690 | B2 | 10/2022 | Szeto |
| 2002/0095584 | A1* | 7/2002 | Royer ................ H04L 63/168 713/183 |
| 2002/0143533 | A1 | 10/2002 | Lucas et al. |
| 2002/0188896 | A1 | 12/2002 | Filteau |
| 2003/0014284 | A1 | 1/2003 | Jones |
| 2003/0028368 | A1 | 2/2003 | Grandy |
| 2003/0055679 | A1 | 3/2003 | Soll |
| 2004/0030584 | A1 | 2/2004 | Harris |
| 2004/0111296 | A1 | 6/2004 | Rosenfeld |
| 2005/0010098 | A1 | 1/2005 | Frigstad et al. |
| 2005/0033121 | A1 | 2/2005 | Modrovich |
| 2005/0108267 | A1 | 5/2005 | Gibson et al. |
| 2006/0171573 | A1 | 8/2006 | Rogers |
| 2006/0212484 | A1 | 9/2006 | Chaffin, Jr. |
| 2006/0242143 | A1 | 10/2006 | Esham |
| 2007/0133852 | A1 | 6/2007 | Collins et al. |
| 2007/0143150 | A1 | 6/2007 | Sasai |
| 2007/0237378 | A1 | 10/2007 | Reiner |
| 2007/0270695 | A1 | 11/2007 | Keen |
| 2009/0138284 | A1 | 5/2009 | Guadagna et al. |
| 2010/0114597 | A1 | 5/2010 | Shreiber et al. |
| 2010/0138231 | A1* | 6/2010 | Linthicum ............ G16H 80/00 715/764 |
| 2010/0138239 | A1 | 6/2010 | Reicher |
| 2010/0191546 | A1 | 7/2010 | Kanamarlapudi et al. |
| 2011/0099024 | A1* | 4/2011 | Lee ........................ G16H 50/20 705/2 |
| 2011/0112867 | A1* | 5/2011 | Menschik ............... G06F 16/68 705/3 |
| 2012/0030151 | A1 | 2/2012 | Huang et al. |
| 2012/0069131 | A1* | 3/2012 | Abelow ............ G06Q 30/0601 345/589 |
| 2014/0280496 | A1 | 9/2014 | Owens et al. |
| 2015/0006192 | A1 | 1/2015 | Sudharsan et al. |
| 2015/0134826 | A1 | 5/2015 | Shah et al. |
| 2015/0278443 | A1 | 10/2015 | Bogaert et al. |
| 2016/0012030 | A1 | 1/2016 | Tran |
| 2016/0042146 | A1 | 2/2016 | Douglass et al. |
| 2016/0099842 | A1 | 4/2016 | Krishnamoorthy et al. |
| 2016/0132572 | A1 | 5/2016 | Chang |
| 2016/0328517 | A1 | 11/2016 | Deng et al. |
| 2017/0093872 | A1 | 3/2017 | Braksator |
| 2018/0060512 | A1 | 3/2018 | Sorenson et al. |
| 2018/0137244 | A1 | 5/2018 | Sorenson |
| 2018/0176078 | A1 | 6/2018 | Nigro |
| 2018/0197624 | A1 | 7/2018 | Robaina |
| 2018/0225673 | A1 | 8/2018 | Dubey |
| 2018/0342050 | A1 | 11/2018 | Fitzgerald et al. |
| 2018/0358123 | A1 | 12/2018 | Silver |
| 2018/0359256 | A1 | 12/2018 | Luzader |
| 2019/0018694 | A1 | 1/2019 | Rhodes et al. |
| 2019/0096060 | A1 | 3/2019 | Zhang et al. |
| 2019/0114766 | A1 | 4/2019 | Song et al. |
| 2019/0138693 | A1 | 5/2019 | Muller et al. |
| 2019/0147507 | A1 | 5/2019 | Lukacsko et al. |
| 2019/0156921 | A1 | 5/2019 | Kohli |
| 2019/0171914 | A1 | 6/2019 | Zlotnick et al. |
| 2019/0333274 | A1 | 10/2019 | Brown |
| 2019/0340468 | A1 | 11/2019 | Stumpe et al. |
| 2019/0354882 | A1 | 11/2019 | Sharma et al. |
| 2019/0371438 | A1 | 12/2019 | Chintamaneni |
| 2020/0202863 | A1* | 6/2020 | Paul ........................ G10L 15/26 |
| 2020/0251225 | A1 | 8/2020 | Murrish et al. |
| 2020/0286405 | A1 | 9/2020 | Buras et al. |
| 2020/0303048 | A1 | 9/2020 | Petri et al. |
| 2020/0335188 | A1 | 10/2020 | Ozeran |
| 2020/0381108 | A1* | 12/2020 | Ahmad .................. G06Q 40/12 |
| 2020/0398083 | A1 | 12/2020 | Adelsheim |
| 2021/0074427 | A1 | 3/2021 | Xu et al. |
| 2021/0090717 | A1* | 3/2021 | Manuel ................. G06F 16/955 |
| 2021/0158933 | A1* | 5/2021 | Frosch .................. G16H 30/40 |
| 2021/0183498 | A1 | 6/2021 | Kalafut et al. |
| 2021/0256694 | A1 | 8/2021 | Min |
| 2022/0051771 | A1 | 2/2022 | Lyman et al. |
| 2022/0084645 | A1 | 3/2022 | Ginsburg |
| 2022/0137921 | A1* | 5/2022 | Rubin ................... G16H 40/20 704/275 |
| 2022/0138411 | A1* | 5/2022 | Rubin ................... G16H 40/20 715/224 |
| 2022/0139509 | A1* | 5/2022 | Rubin ................... G16H 10/60 705/2 |
| 2022/0139513 | A1* | 5/2022 | Rubin ................... G16H 15/00 705/3 |
| 2022/0139514 | A1* | 5/2022 | Rubin ................... G16H 15/00 705/2 |
| 2022/0139515 | A1* | 5/2022 | Rubin ................... G06F 16/258 705/2 |
| 2022/0139571 | A1* | 5/2022 | Rubin ................... H04L 67/00 705/2 |
| 2022/0141288 | A1* | 5/2022 | Rubin ................... H04L 67/00 709/204 |
| 2022/0157425 | A1 | 5/2022 | Vemula |
| 2022/0199211 | A1 | 6/2022 | Wunderink et al. |
| 2022/0199212 | A1 | 6/2022 | Wunderink et al. |
| 2022/0199262 | A1 | 6/2022 | Wunderink et al. |
| 2022/0254517 | A1* | 8/2022 | Jancsary ............... G16H 30/40 |
| 2022/0270085 | A1 | 8/2022 | Mee |

(56) References Cited

U.S. PATENT DOCUMENTS

| | | | |
|---|---|---|---|
| 2023/0042272 A1* | 2/2023 | Mahadeva Cadwell | ................... G16H 10/60 |
| 2023/0326615 A1 | 10/2023 | Joao | |

FOREIGN PATENT DOCUMENTS

| | | | |
|---|---|---|---|
| EP | 2996058 | A1 | 3/2016 |
| EP | 4026136 | A1 | 7/2022 |
| JP | 2005202507 | A | 7/2005 |
| WO | 0177896 | A1 | 10/2001 |
| WO | 03040990 | A2 | 5/2003 |
| WO | 2006094032 | A2 | 9/2006 |
| WO | 2009073185 | A1 | 6/2009 |
| WO | 2018065613 | A1 | 4/2018 |
| WO | 2018073707 | A1 | 4/2018 |
| WO | 2019051359 | A1 | 3/2019 |
| WO | 2020093165 | A1 | 5/2020 |
| WO | 2020178687 | A1 | 9/2020 |
| WO | 2022212771 | A2 | 10/2022 |

OTHER PUBLICATIONS

"Final Office Action Issued in U.S. Appl. No. 17/518,451", Mailed Date: Feb. 7, 2023, 28 Pages.

"Non Final Office Action Issued in U.S. Appl. No. 17/518,457", Mailed Date: Mar. 31, 2023, 11 Pages.

"Non Final Office Action Issued in U.S. Appl. No. 17/518,451", Mailed Date: Jul. 21, 2022, 24 Pages.

"Final Office Action Issued in U.S. Appl. No. 17/524,340", Mailed Date: May 13, 2022, 17 Pages.

"Non Final Office Action Issued in U.S. Appl. No. 17/524,340", Mailed Date: Jan. 26, 2022, 15 Pages.

Gao, et al., "New Frontiers: An Update on Computer-Aided Diagnosis for Breast Imaging in the Age of Artificial Intelligence", In American Journal of Roentgenology, vol. 212, Issue 2, Feb. 2018, 18 Pages.

"International Search Report and Written Opinion Issued In PCT Application No. PCT/US21/058943", Mailed Date: Feb. 2, 2022, 9 Pages.

"International Search Report and Written Opinion Issued in PCT Application No. PCT/US21/064665", Mailed Date: Mar. 17, 2022, 7 Pages.

"International Search Report and Written Opinion Issued in PCT Application No. PCT/US21/064675", Malled Date: Mar. 16, 2022, 7 Pages.

"International Search Report and Written Opinion Issued in PCT Application No. PCT/US21/064684", Mailed Date: Mar. 9, 2022, 7 Pages.

"Non Final Office Action Issued in U.S. Appl. No. 17/518,457", Mailed Date: Jul. 22, 2022, 12 Pages.

"Non Final Office Action Issued in U.S. Appl. No. 17/524,340", Mailed Date: Sep. 15, 2022, 18 Pages.

"Final Office Action Issued in U.S. Appl. No. 17/518,457", Mailed Date: Nov. 28, 2022, 21 Pages.

"Final Office Action Issued in U.S. Appl. No. 17/518,457", Mailed Date: Oct. 12, 2023, 12 Pages.

"Non Final Office Action Issued in U.S. Appl. No. 17/518,443", Mailed Date: Jul. 11, 2023, 32 Pages.

"Non Final Office Action Issued in U.S. Appl. No. 17/518,451", Mailed Date: Aug. 2, 2023, 24 Pages.

Final Office Action Issued in U.S. Appl. No. 17/524,340, Mailed Date: Dec. 27, 2022 19 Pages.

Final Office Action mailed on Feb. 2, 2024, in U.S. Appl. No. 17/518,443, 24 pages.

Final Office Action mailed on Mar. 13, 2024, in U.S. Appl. No. 17/518,479, 23 pages.

Final Office Action mailed on Mar. 14, 2024, in U.S. Appl. No. 17/518,488, 21 pages.

Hosny, et al., "Artificial intelligence in radiology.", Nature Reviews Cancer, vol. 18, No. 8, 2018, pp. 500-510.

Non-final Office Action mailed on Dec. 21, 2023, in U.S. Appl. No. 17/558,277, 31 pages.

Non-Final Office Action mailed on Dec. 21, 2023, in U.S. Appl. No. 17/558,319, 31 pages.

Non-Final Office Action mailed on Dec. 29, 2023, in U.S. Appl. No. 17/518,492 , 16 pages.

Non-Final Office Action mailed on Feb. 15, 2024, in U.S. Appl. No. 17/518,457, 16 pages.

Non-Final Office Action mailed on Jan. 18, 2024, in U.S. Appl. No. 17/558,336, 26 pages.

Non-Final Office Action mailed on Nov. 9, 2023, in U.S. Appl. No. 17/518,464, 32 pages.

Non-Final Office Action mailed on Nov. 16, 2023, in U.S. Appl. No. 17/518,488, 18 pages.

Non-Final Office Action mailed on Nov. 22, 2023, in U.S. Appl. No. 17/518,479, 17 pages.

Notice of Allowance mailed on Dec. 1, 2023, in U.S. Appl. No. 17/518,451, 14 Pages.

Notice of Allowance mailed on Dec. 14, 2023, in U.S. Appl. No. 17/518,451, 10 pages.

Notice of Allowance mailed on Mar. 5, 2024, in U.S. Appl. No. 17/518,451, 02 pages.

Notice of Allowance mailed on Feb. 1, 2024, in U.S. Appl. No. 17/518,451, 03 pages.

Notice of Allowance mailed on Feb. 14, 2024, in U.S. Appl. No. 17/518,451, 3 pages.

Notice of Allowance mailed on Feb. 28, 2024, in U.S. Appl. No. 17/518,451, 03 pages.

Notice of Allowance mailed on Jan. 24, 2024, in U.S. Appl. No. 17/518,451, 3 pages.

Final Office Action mailed on May 16, 2024, in U.S. Appl. No. 17/518,464, 34 pages.

Non-Final Office Action issued in U.S. Appl. No. 17/518,443, mailed on May 24, 2024, 16 Pages.

Non-Final Office Action mailed on Aug. 29, 2024, in U.S. Appl. No. 17/518,488, 31 pages.

Final Office Action issued in U.S. Appl. No. 17/518,492, mailed on Sep. 18, 2024, 12 Pages.

Final Office Action mailed on Sep. 11, 2024, in U.S. Appl. No. 17/558,277, 37 pages.

Final Office Action mailed on Sep. 12, 2024, in U.S. Appl. No. 17/558,336, 30 pages.

Non-Final Office Action mailed on Sep. 20, 2024, in U.S. Appl. No. 17/518,464, 43 pages.

U.S. Appl. No. 17/518, 464,filed Nov. 3, 2021.
U.S. Appl. No. 17/518,457, filed Nov. 3, 2021.
U.S. Appl. No. 17/524,340, filed Nov. 11, 2021.
U.S. Appl. No. 17/558,319, filed Dec. 21, 2021.
U.S. Appl. No. 17/518,492, filed Nov. 3, 2021.
U.S. Appl. No. 17/518,443, filed Nov. 3, 2021.
U.S. Appl. No. 17/518,451, filed Nov. 3, 2021.
U.S. Appl. No. 17/518,479, filed Nov. 3, 2021.
U.S. Appl. No. 17/518,488, filed Nov. 3, 2021.
U.S. Appl. No. 17/558,277, filed Dec. 21, 2021.
U.S. Appl. No. 17/558,336, filed Dec. 21, 2021.

Final office action mailed on Sep. 25, 2024, in U.S. Appl. No. 17/518,457, 13 pages.

Non- Final Office Action mailed on Sep. 28, 2024, in U.S. Appl. No. 17/518,479, 20 pages.

\* cited by examiner

COMMUNICATION SYSTEM AND METHOD

RELATED APPLICATION(S)

This application claims the benefit of U.S. Provisional Application No. 63/109,219, filed on 3 Nov. 2020, 63/113,439, filed on 13 Nov. 2020, and 63/129,301, filed on 22 Dec. 2020; the entire contents of which is herein incorporated by reference.

TECHNICAL FIELD

This disclosure relates to communication systems and methods and, more particularly, to communications systems and methods that enable the interoperation of disparate systems.

BACKGROUND

As is known in the art, medical processionals may use various computer systems to review various pieces of medical information. For example, a first computer system may be used to review medical images, a second computer system may be used to review medical records, and a third computer system may be used to generate a medical report based upon their review of e.g., medical images or medical records.

Unfortunately, these disparate systems tend to be technological islands that are generally incapable of exchanging meaningful data between these systems. Accordingly and when generating such a medical report, findings made in one system may need to be manually reentered into another system.

SUMMARY OF DISCLOSURE

In one implementation, a computer-implemented method is executed on a computing system and includes: defining a communication computing system within a computing network, wherein the computing network includes a plurality of disparate platforms configured to provide information concerning various topics; enabling a user to issue a verbal command concerning one or more of the plurality of disparate platforms; processing the verbal command to generate a platform-useable command based, at least in part, upon the verbal command; and providing the platform-useable command to at least a portion of the plurality of disparate platforms via the communication computing system.

One or more of the following features may be included. The plurality of disparate platforms may include a plurality of disparate medical platforms. The plurality of disparate medical platforms may include one or more of: a medical imaging platform; a medical report platform; a medical analysis platform; a medical record platform; and a conversational AI platform. The information concerning various topics may include information concerning various patients. The communication computing system may include a cloud-based communication computing system. At least a portion of the plurality of disparate platforms may be executed on a single computing system. Processing the verbal command to generate a platform-useable command based, at least in part, upon the verbal command may include: processing the verbal command via a conversational AI platform to generate the platform-useable command based, at least in part, upon the verbal command. Providing the platform-useable command to at least a portion of the plurality of disparate platforms via the communication computing system may include: receiving the platform-useable command on the communication computing system. Providing the platform-useable command to at least a portion of the plurality of disparate platforms via the communication computing system further may include: broadcasting the platform-useable command to at least a portion of the plurality of disparate platforms. The platform-useable command may be received on at least one of the plurality of disparate platforms. The platform-useable command may be processed on the at least one of the plurality of disparate platforms.

In another implementation, a computer program product resides on a computer readable medium and has a plurality of instructions stored on it. When executed by a processor, the instructions cause the processor to perform operations including: defining a communication computing system within a computing network, wherein the computing network includes a plurality of disparate platforms configured to provide information concerning various topics; enabling a user to issue a verbal command concerning one or more of the plurality of disparate platforms; processing the verbal command to generate a platform-useable command based, at least in part, upon the verbal command; and providing the platform-useable command to at least a portion of the plurality of disparate platforms via the communication computing system.

One or more of the following features may be included. The plurality of disparate platforms may include a plurality of disparate medical platforms. The plurality of disparate medical platforms may include one or more of: a medical imaging platform; a medical report platform; a medical analysis platform; a medical record platform; and a conversational AI platform. The information concerning various topics may include information concerning various patients. The communication computing system may include a cloud-based communication computing system. At least a portion of the plurality of disparate platforms may be executed on a single computing system. Processing the verbal command to generate a platform-useable command based, at least in part, upon the verbal command may include: processing the verbal command via a conversational AI platform to generate the platform-useable command based, at least in part, upon the verbal command. Providing the platform-useable command to at least a portion of the plurality of disparate platforms via the communication computing system may include: receiving the platform-useable command on the communication computing system. Providing the platform-useable command to at least a portion of the plurality of disparate platforms via the communication computing system further may include: broadcasting the platform-useable command to at least a portion of the plurality of disparate platforms. The platform-useable command may be received on at least one of the plurality of disparate platforms. The platform-useable command may be processed on the at least one of the plurality of disparate platforms.

In another implementation, a computing system includes a processor and memory is configured to perform operations including: defining a communication computing system within a computing network, wherein the computing network includes a plurality of disparate platforms configured to provide information concerning various topics; enabling a user to issue a verbal command concerning one or more of the plurality of disparate platforms; processing the verbal command to generate a platform-useable command based, at least in part, upon the verbal command; and providing the platform-useable command to at least a portion of the plurality of disparate platforms via the communication computing system.

One or more of the following features may be included. The plurality of disparate platforms may include a plurality of disparate medical platforms. The plurality of disparate medical platforms may include one or more of: a medical imaging platform; a medical report platform; a medical analysis platform; a medical record platform; and a conversational AI platform. The information concerning various topics may include information concerning various patients. The communication computing system may include a cloud-based communication computing system. At least a portion of the plurality of disparate platforms may be executed on a single computing system. Processing the verbal command to generate a platform-useable command based, at least in part, upon the verbal command may include: processing the verbal command via a conversational AI platform to generate the platform-useable command based, at least in part, upon the verbal command. Providing the platform-useable command to at least a portion of the plurality of disparate platforms via the communication computing system may include: receiving the platform-useable command on the communication computing system. Providing the platform-useable command to at least a portion of the plurality of disparate platforms via the communication computing system further may include: broadcasting the platform-useable command to at least a portion of the plurality of disparate platforms. The platform-useable command may be received on at least one of the plurality of disparate platforms. The platform-useable command may be processed on the at least one of the plurality of disparate platforms.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
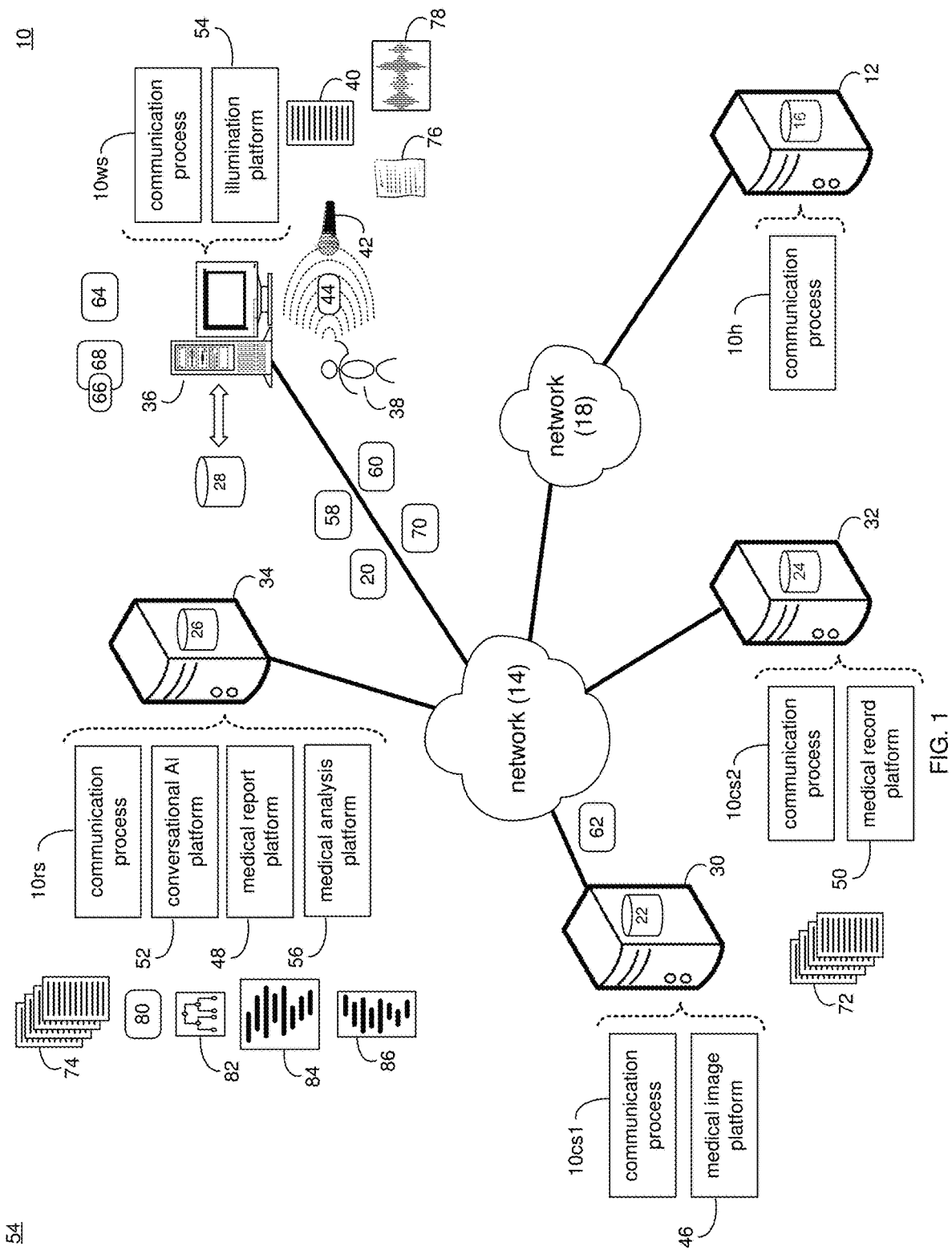
FIG. 1 is a diagrammatic view of a plurality of disparate systems that communicate via a communication process coupled to a distributed computing network.

Referring to FIG. 1, there is shown communication process 10. As will be discussed below in greater detail, communication process 10 may be configured to allow for the communication and transfer of data between various disparate systems.

Communication process 10 may be implemented as a server-side process, a client-side process, or a hybrid server-side/client-side process. For example, communication process 10 may be implemented as a purely server-side process via communication process 10$h$. Alternatively, communication process 10 may be implemented as a purely client-side process via one or more of communication process 10$cs$1, communication process 10$cs$2, communication process 10$rs$, and communication process 10$ws$. Alternatively still, communication process 10 may be implemented as a hybrid server-side/client-side process via communication process 10$h$ in combination with one or more of communication process 10$cs$1, communication process 10$cs$2, communication process 10$rs$, and communication process 10$ws$.

Accordingly, communication process 10 as used in this disclosure may include any combination of communication process 10$h$, communication process 10$cs$1, communication process 10$cs$2, communication process 10$rs$, and communication process 10$ws$.

Communication process 10$h$ may be a server application and may reside on and may be executed by communication computing system 12, which may be connected to network 14 (e.g., the Internet or a local area network). Communication computing system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of communication computing system 12 may execute one or more operating systems, examples of which may include but are not limited to: Microsoft Windows Server™; Redhat Linux™, Unix, or a custom operating system, for example.

The instruction sets and subroutines of communication process 10$h$, which may be stored on storage device 16 coupled to communication computing system 12, may be executed by one or more processors (not shown) and one or more memory architectures (not shown) included within communication computing system 12. Examples of storage device 16 may include but are not limited to: a hard disk drive; a RAID device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; an intranet; or the internet. Accordingly, network 14 may be a local area network and network 18 may be the internet, thus allowing communication process 10h to be a cloud-based resource.

Various pieces of data (e.g. data 20) may be transferred between communication process 10h, communication process 10cs1, communication process 10cs2, communication process 10rs, and communication process 10ws. Examples of data 20 may include but are not limited to data requests (e.g., data read requests and data write requests) and the related data itself.

The instruction sets and subroutines of communication process 10cs1, communication process 10cs2, communication process 10rs, and communication process 10ws, which may be stored on storage devices 22, 24, 26, 28 (respectively) coupled to computing systems 30, 32, 34, 36 (respectively), may be executed by one or more processors (not shown) and one or more memory architectures (not shown) incorporated into computing systems 30, 32, 34, 36 (respectively). Examples of storage devices 22, 24, 26, 28 may include but are not limited to: hard disk drives; optical drives; RAID devices; random access memories (RAM); read-only memories (ROM), and all forms of flash memory storage devices. Examples of computing systems 30, 32, 34, 36 may include, but are not limited to, collaborating computing system 30 (e.g., a personal computer, a workstation computer, a server computer, and a cloud-based resource), collaborating computing system 32 (e.g., a personal computer, a workstation computer, a server computer, and a cloud-based resource), report computing system 34 (e.g., a personal computer, a workstation computer, a server computer, and a cloud-based resource), and workstation computing system 36 (e.g., a smart telephone, a tablet computer, a notebook computer, a laptop computer, a personal computer, a workstation computer, a server computer, and a cloud-based resource).

As will be discussed below in greater detail, the above-described platform (e.g., communication process 10 in combination with computing systems 12, 30, 32, 34, 36) may be configured to allow clinician 38 (e.g., a radiologist, a cardiologist or a pathologist) to review medical information (e.g., data 20) and populate medical report 40. The medical information (e.g., data 20) may be provided by one or more of the collaborating systems (e.g., collaborating computing systems 30, 32), examples of which may include but are not limited to a collaborating system executing a PACS system and a collaborating system executing an EHR system.

As is known in the art, a PACS (Picture Archiving and Communication System) system is a medical imaging technology that provides economical storage and convenient access to images from multiple modalities (source machine types). Electronic images and reports may be transmitted digitally via PACS; thus eliminating the need to manually file, retrieve and/or transport film jackets. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM.

As is known in the art, an EHR (Electronic Health Record) system is a systematized collection of patient and population electronically stored health information in a digital format. These records may be shared across different health care settings, wherein records may be shared through network-connected, enterprise-wide information systems or other information networks and exchanges. An EHR system may define a range of data, including demographics, medical histories, medications and allergies, immunization status, laboratory test results, radiology images, vital signs, personal statistics, and billing information.

Accordingly and as will be discussed below in greater detail, clinician 38 may utilize workstation computing system 36 to review medical information (e.g., data 20) provided by the collaborating systems (e.g., collaborating computing systems 30, 32). Report computing system 34 may be configured to allow clinician 38 to populate medical report (e.g., medical report 40). Communication process 10 may be configured to allow clinician 38 to utilize audio input device 42 to provide verbal information/command 44 based upon information ascertained from the medical information (e.g., data 20).

Examples of audio input device 42 may include but are not limited to a lapel microphone, a desktop microphone, a wall-mounted microphone, or a device-embedded microphone (e.g., a microphone embedded into a laptop computer). As will be discussed below in greater detail, communication computing system 12 may be configured to allow all of the computing systems (e.g., computing systems 12, 30, 32, 34, 36) within the above-described platform to communicate with each other and exchange information (e.g., data 20).

General Intersystem Communication

Figure 2:
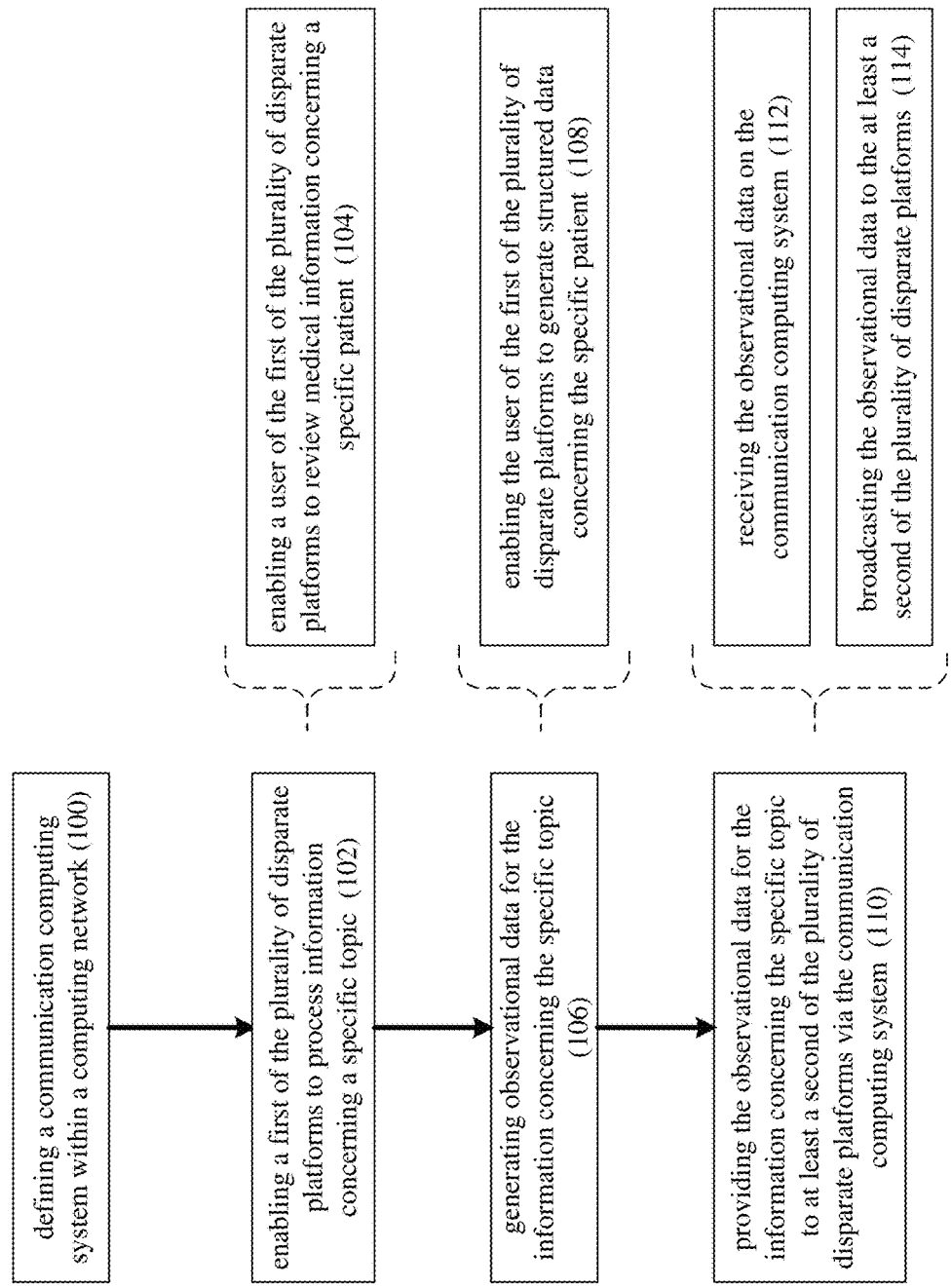
FIG. 2 is a flow chart of one implementation of the communication process of FIG. 1 according to an implementation of this disclosure.

Referring also to FIG. 2, communication process 10 may define 100 a communication computing system (e.g., communication computing system 12) within a computing network (e.g., network 14 and/or network 18). The communication computing system (e.g., communication computing system 12) may be configured as a local system or as a remote system. For example, communication computing system 12 may be a local computing system directly coupled to e.g., computing systems 30, 32, 34, 36 via a local area network (e.g., network 14). Additionally/alternatively, communication computing system 12 may be a cloud-based computing system (e.g., a cloud-based resource) indirectly coupled to e.g., computing systems 30, 32, 34, 36 via network 18 (e.g., the internet). As will be discussed below in greater detail, communication computing system 12 (in combination with communication process 10) may be configured to effectuate communication between computing systems 30, 32, 34, 36.

As discussed above, this computing network (e.g., network 14 and/or network 18) may couple various computing systems (e.g., computing systems 12, 30, 32, 34, 36) configured to provide information (e.g., data 20) concerning various topics. Disparate platforms executed on these computing systems (e.g., computing systems 12, 30, 32, 34, 36) may generate and/or modify information (e.g., data 20), which may be provided to other computing systems within the computing network (e.g., network 14 and/or network 18). For example, a disparate platform executed on collaborating computing system 30 may generate information (e.g., data 20) that may be provided to workstation computing system 36 via the computing network (e.g., network 14 and/or network 18).

As discussed above, communication process 10 may be configured to allow clinician 38 (e.g., a radiologist, a cardiologist or a pathologist) to utilize workstation computing system 36 to review medical information (e.g., data 20) concerning various patients and populate various medical reports (e.g., medical report 40). Accordingly, the plurality of disparate platforms executed on these computing systems (e.g., computing systems 12, 30, 32, 34, 36) may include a plurality of disparate medical platforms (e.g., medical imaging platform 46; medical report platform 48; medical record platform 50; conversational AI platform 52; illumination platform 54 and/or medical analysis platform 56.

At least a portion of the plurality of disparate platforms (e.g., disparate platforms 46, 48, 50, 52, 54, 56) may be executed on a single computing system. For example and referring also to FIG. 3, workstation computing system 36 may be configured to support multiple monitors (e.g., monitors 150, 152, 154), which may be simultaneously used by clinician 38 to access and utilize the various disparate platforms (e.g., disparate platforms 46, 48, 50, 52, 54, 56).

In this example, monitor 150 is shown to allow clinician 38 to access medical imaging platform 46, wherein monitor 152 is shown to allow clinician 38 to access medical record platform 50. Assume for this example that medical imaging platform 46 is being executed on collaborating system 30, while medical record platform 50 is being executed on collaborating system 32. Accordingly, at least a portion of medical imaging platform 46 and at least a portion of medical record platform 50 may be executed on a single computing system (e.g., workstation computing system 36), wherein:

medical image platform portion 156 may interact with medical image platform 46 being executed on collaborating system 30 and may enable clinician 38 to review the medical images provided by medical image platform 46 on workstation computing system 36; and medical record platform portion 158 may interact with medical record platform 50 being executed on collaborating system 32 and may enable clinician 38 to review the medical records provided by medical record platform 50 on workstation computing system 36.

A) Passing of Observational Data

Communication process 10 may enable 102 a first of the plurality of disparate platforms (e.g., medical image platform 46) to process information (e.g., data 20) concerning a specific topic.

As discussed above, communication process 10 may be configured to allow clinician 38 (e.g., a radiologist, a cardiologist or a pathologist) to utilize workstation computing system 36 to review medical information (e.g., data 20) concerning various patients and populate various medical reports (e.g., medical report 40). Accordingly and when enabling 102 a first of the plurality of disparate platforms (e.g., medical image platform 46) to process information (e.g., data 20) concerning a specific topic (e.g., a specific patient), communication process 10 may enable 104 a user (e.g., clinician 38) of the first of the plurality of disparate platforms (e.g., medical image platform 46) to review medical information (e.g., data 20) concerning a specific patient.

For this example, assume that collaborating system 30 is executing medical image platform 46 (e.g., PACS), wherein medical image platform portion 156 is executed on workstation computing system 36. Accordingly, medical image platform 46 (e.g., PACS) being executed on collaborating system 30 may provide chest x-ray image 160 (e.g., data 20) of a patient (e.g., patient John Smith), wherein clinician 38 may review chest x-ray image 160 using medical image platform portion 156 being executed on workstation computing system 36.

Communication process 10 may generate 106 observational data (e.g., data 58) for the information (e.g., data 20) concerning the specific topic (e.g., a specific patient). For example and when generating 106 observational data (e.g., data 58) for the information (e.g., data 20) concerning the specific topic (e.g., a specific patient), communication process 10 may enable 108 the user (e.g., clinician 38) of the first of the plurality of disparate platforms (e.g., medical image platform 46) to generate structured data concerning the specific patient.

Specifically and with respect to structured data, structured data may relate to a structured observation that is made by (in this example) clinician 38, wherein a structured observation may be codified (have one or more medical codes assigned). For example, a lung may have an assigned medical code . . . and a growth may have an assigned medical code . . . and over 5.0 centimeters may have an assigned medical code.

Accordingly, communication process 10 may enable 104 clinician 38 to review chest x-ray image 160 (via medical image platform portion 156 executed on workstation computing system 36) to generate 106 observational data (e.g., data 58) for chest x-ray image 160 of patient John Smith. Examples of such observational data (e.g., data 58) may include but are not limited to structured data that concerns e.g., measurements of objects within an image (e.g., x-ray image 160), the location of objects within an image (e.g., x-ray image 160), and the type of image (e.g., x-ray image 160).

Accordingly and via medical image platform portion 156 executed on workstation computing system 36, clinician 38 may review chest x-ray image 160. Upon reviewing chest x-ray image 160, clinician 38 may notice a growth (e.g., growth 162) within x-ray image 160. Accordingly and through medical image platform portion 156 executed on workstation computing system 36, communication process 10 may enable 108 clinician 38 to measure growth 162 (measured to be 5.1 centimeters), thus generating 106 observational data (e.g., data 58).

Communication process 10 may provide 110 the observational data (e.g., data 58) for the information (e.g., data 20) concerning the specific topic (e.g., a specific patient) to at least a second of the plurality of disparate platforms (e.g., medical report platform 48) via the communication computing system (e.g., communication computing system 12). For this example, assume that the observational data (e.g., data 58) identifies the location of growth 162 (e.g., lower quadrant of left lung) and the size of growth 162 (e.g., 5.1 centimeters).

When providing 110 the observational data (e.g., data 58) for the information (e.g., data 20) concerning the specific topic (e.g., a specific patient) to at least a second of the plurality of disparate platforms (e.g., medical report platform 48) via the communication computing system (e.g., communication computing system 12), communication process 10 may:

receive 112 the observational data (e.g., data 58) on the communication computing system (e.g., communication computing system 12); and broadcast 114 the observational data (e.g., data 58) to the at least a second of the plurality of disparate platforms (e.g., medical report platform 48).

For example and as discussed above, through medical image platform portion 156 executed on workstation computing system 36, communication process 10 may enable 108 clinician 38 to measure growth 162 (measured to be 5.1 centimeters), thus generating 106 observational data (e.g., data 58). This observational data (e.g., data 58) may then be provided to communication computing system 12. For example, medical image platform portion 156 that is executed on workstation computing system 36 may provide observational data (e.g., data 58) to communication computing system 12. Additionally/alternatively, medical image platform 46 (e.g., PACS) that is executed on collaborating system 30 may provide observational data (e.g., data 58) to communication computing system 12.

Once the observational data (e.g., data 58) is received 112 on the communication computing system (e.g., communication computing system 12), the communication computing system (e.g., communication computing system 12) may broadcast 114 the observational data (e.g., data 58) to the at least a second of the plurality of disparate platforms (e.g., medical report platform 48).

As discussed above, medical report platform 48 may be configured to allow clinician 38 to populate a medical report (e.g., medical report 40) concerning (in this example) patient John Smith. Accordingly and as will be discussed below in greater detail, once the observational data (e.g., data 58) is received 112, the communication computing system (e.g., communication computing system 12) may broadcast 114 the observational data (e.g., data 58) to medical report platform 48 so that the observational data (e.g., data 58) may be utilized to populate a medical report (e.g., medical report 40) for the patient (e.g., patient John Smith). Accordingly, the appropriate field (e.g., field 164) within medical report 40 of patient John Smith may be populated by medical report platform 48 to state that chest x-ray image 160 of patient John Smith shows a 5.1 centimeter growth (e.g., growth 162) in the lower quadrant of the left lung.

B) Processing of Verbal Commands

Figure 4:
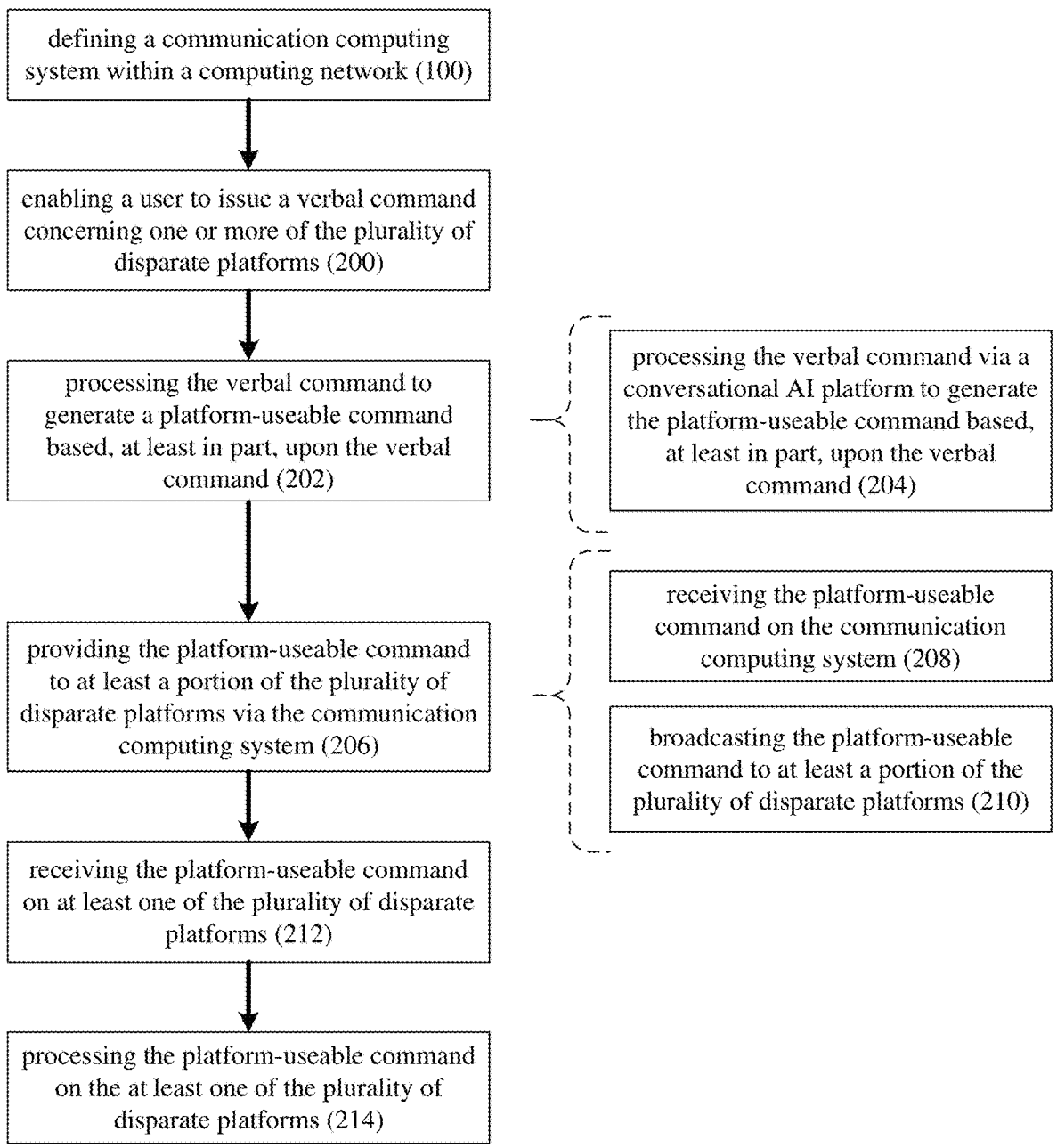
FIG. 4 is a flow chart of another implementation of the communication process of FIG. 1 according to an implementation of this disclosure.

Referring also to FIG. 4 and as discussed above, communication process 10 may define 100 a communication computing system (e.g., communication computing system 12) within a computing network (e.g., network 14 and/or network 18). This computing network (e.g., network 14 and/or network 18) may couple various computing systems (e.g., computing systems 12, 30, 32, 34, 36) configured to provide information (e.g., data 20) concerning various topics. Disparate platforms (e.g., disparate platforms 46, 48, 50, 52, 54, 56) executed on these computing systems (e.g., computing systems 12, 30, 32, 34, 36) may generate and/or modify information (e.g., data 20), which may be provided to other computing systems within the computing network (e.g., network 14 and/or network 18).

Communication process 10 may enable 200 a user (e.g., clinician 38) to issue a verbal command (e.g., verbal information/command 44) concerning one or more of the plurality of disparate platforms (e.g., disparate platforms 46, 48, 50, 52, 54, 56).

As discussed above, communication process 10 may be configured to allow clinician 38 to utilize audio input device 42 to provide verbal information/command 44 based upon information ascertained from the medical information (e.g., data 20). Examples of audio input device 42 may include but are not limited to a lapel microphone, a desktop microphone, a wall-mounted microphone, or a device-embedded microphone (e.g., a microphone embedded into a laptop computer). Accordingly, since communication process 10 enables 200 clinician 38 to issue verbal commands (e.g., verbal information/command 44) concerning the disparate platforms (e.g., disparate platforms 46, 48, 50, 52, 54, 56), communication process 10 may provide clinician 38 with virtual assistant functionality.

Communication process 10 may process 202 the verbal command (e.g., verbal information/command 44) to generate a platform-useable command (e.g., platform-useable command 60) based, at least in part, upon the verbal command (e.g., verbal information/command 44). As discussed above, the plurality of disparate platforms (e.g., disparate platforms 46, 48, 50, 52, 54, 56) may include medical imaging platform 46; medical report platform 48; medical record platform 50; conversational AI platform 52; illumination platform 54 and/or medical analysis platform 56.

When processing 202 the verbal command (e.g., verbal information/command 44) to generate a platform-useable command (e.g., platform-useable command 60) based, at least in part, upon the verbal command (e.g., verbal information/command 44), communication process 10 may process 204 the verbal command (e.g., verbal information/command 44) via a conversational AI platform (e.g., conversational AI platform 52) to generate the platform-useable command (e.g., platform-useable command 60) based, at least in part, upon the verbal command (e.g., verbal information/command 44).

While conversational AI platform 52 is shown to be executed on report computing system 34, this is for illustrative purposes only and is not intended to be a limitation of this disclosure, as other configurations are possible and are considered to be within the scope of this disclosure. For example, conversational AI platform 52 may be executed on any other computing system (e.g., computing systems 12, 30, 32, 36), As is known in the art, conversational AI is a technology that enables speech-based interaction between humans and computing systems. Accordingly, conversational AI platform 52 may process human speech (e.g., verbal information/command 44) to decipher the same so that e.g., a computing system may effectuate a computer-based response and/or render a speech-based response.

Conversational AI platform 52 may utilize Natural language Understanding (NLU). As is known in the art, NLU is a branch of artificial intelligence (AI) that uses computer software to understand verbal inputs provided by a user (e.g., clinician 38). NLU may directly enable human-computer interaction (HCI), wherein the understanding of natural human language may enable computers to understand human-provided commands (without the formalized syntax of computer languages) and further enable these computers to respond to the human in their own language. The field of NLU is an important and challenging subset of natural language processing (NLP), as NLU is tasked with communicating with untrained individuals and understanding their intent. Accordingly, NLU goes beyond understanding words and actually interprets the meaning of such words. NLU may use algorithms to reduce human speech into a structured ontology, fleshing out such things as intent, timing, locations and sentiments.

Once generated, communication process 10 may provide 206 the platform-useable command (e.g., platform-useable command 60) to at least a portion of the plurality of disparate platforms (e.g., disparate platforms 46, 48, 50, 52, 54, 56) via the communication computing system (e.g., communication computing system 12).

For the following example, assume that monitor 150 is a diagnostic healthcare display (e.g., such as a healthcare display offered by Barco™). Accordingly, monitor 150 may be controllable by illumination platform 54, which may be executed on workstation computing system 36. Through the use of illumination platform 54, clinician 38 may control various aspects of monitor 150, such as adjusting the brightness, adjusting the contrast, and enabling resolution enhancing features. In order to enable such control of monitor 150, monitor 150 may execute illumination application 166, which may be configured to process commands received from illumination platform 54.

For the following example, assume that verbal information/command 44 provided by clinician 38 is "Hey Monitor . . . Turn on Illuminate", which instructs monitor 150 to turn on a resolution enhancing feature called "Illuminate". Accordingly, communication process 10 (via conversation AI platform) may process 202 verbal information/ command 44 (e.g., "Hey Monitor . . . Turn on Illuminate") to generate a platform-useable command (e.g., platform-useable command 60), wherein an example of platform-useable command 60 may include "Monitor: Illuminate Status=1".

When providing 206 the platform-useable command (e.g., platform-useable command 60) to at least a portion of the plurality of disparate platforms (e.g., disparate platforms 46, 48, 50, 52, 54, 56) via the communication computing system (e.g., communication computing system 12), communication process 10 may:

receive 208 the platform-useable command (e.g., platform-useable command 60) on the communication computing system (e.g., communication computing system 12); and broadcast 210 the platform-useable command (e.g., platform-useable command 60) to at least a portion of the plurality of disparate platforms (e.g., disparate platforms 46, 48, 50, 52, 54, 56).

As discussed above, communication process 10 may enable 200 clinician 38 to issue verbal information/command 44 (e.g., "Hey Monitor . . . Turn on Illuminate"), which may be processed 204 by conversational AI platform 52 (which is executed on report computing system 34) to generate platform-useable command 60 (e.g., Monitor: Illuminate Status=1). Conversational AI platform 52 may then provide platform-useable command 60 to communication computing system 12.

Once the platform-useable command (e.g., platform-useable command 60) is received 208 on the communication computing system (e.g., communication computing system 12), the communication computing system (e.g., communication computing system 12) may broadcast 210 the platform-useable command (e.g., platform-useable command 60) to the a portion of the plurality of disparate platforms (e.g., illumination platform 54).

Once broadcast 210, communication process 10 may receive 212 the platform-useable command (e.g., command 46) on at least one of the plurality of disparate platforms (e.g., computing systems 12, 28, 30, 32, 34). For example, communication process 10 may receive 212 platform-useable command 60 on illumination platform 54 (which is executed on workstation computing system 36). Communication process 10 may then process 214 platform-useable command 60 on illumination platform 54, wherein illumination platform 54 may provide the necessary commands to illumination application 166 (which is executed on monitor 150) so that the Illuminate functionality may be turned on.

In the event that the platform-useable command 60 has some ambiguity, illumination application 166/illumination platform 54 (via communication computing system 12➔conversational AI platform 52) may make an inquiry (possibly verbally) to clarify the ambiguity. For example, if Illuminate has three brightness levels, illumination application 166/illumination platform 54 may verbally ask clinician 38 "What level of brightness would you prefer?"

C) Information Broadcast

Figure 5:
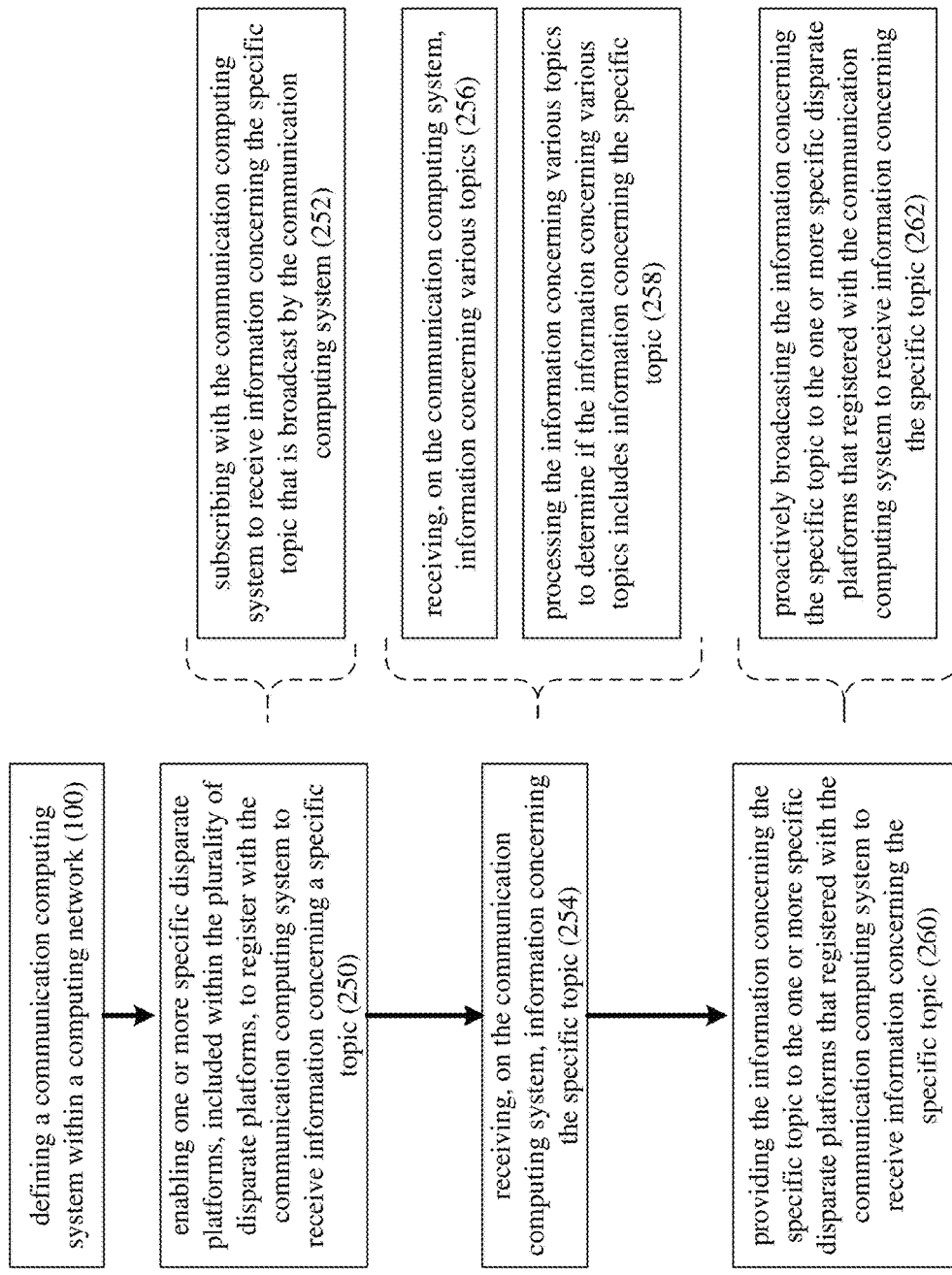
FIG. 5 is a flow chart of another implementation of the communication process of FIG. 1 according to an implementation of this disclosure.

Referring also to FIG. 5 and as discussed above, communication process 10 may define 100 a communication computing system (e.g., communication computing system 12) within a computing network (e.g., network 14 and/or network 18). This computing network (e.g., network 14 and/or network 18) may couple various computing systems (e.g., computing systems 12, 30, 32, 34, 36) configured to provide information (e.g., data 20) concerning various topics. Disparate platforms (e.g., disparate platforms 46, 48, 50, 52, 54, 56) executed on these computing systems (e.g., computing systems 12, 30, 32, 34, 36) may generate and/or modify information (e.g., data 20), which may be provided to other computing systems within the computing network (e.g., network 14 and/or network 18).

As discussed above, communication computing system 12 (in combination with communication process 10) may be configured to effectuate communication between computing systems 30, 32, 34, 36, wherein communication computing system 12 may receive data from one disparate platform and broadcast the data to another disparate platform. As will be discussed below in greater detail, in order to avoid communication computing system 12 broadcasting all data to all disparate platforms, communication process 10 may be configured to enable disparate platforms to register to receive only certain pieces of data.

Communication process 10 may enable 250 one or more specific disparate platforms (e.g., disparate platforms 46, 48, 50, 52, 54, 56), included within the plurality of disparate platforms (e.g., disparate platforms 46, 48, 50, 52, 54, 56), to register with the communication computing system (e.g., communication computing system 12) to receive information (e.g., data 20) concerning a specific topic (e.g., a specific patient).

As discussed above, assume for this example that clinician 38 is using medical image platform 46 (executed on collaborating computing system 30) to review chest x-ray image 160 of patient John Smith, wherein clinician 38 is populating medical report 40 using medical report platform 48 (executed on report computing system 34). Accordingly, medical report platform 48 may be interested in receiving all information that concerns patient John Smith (as clinician 38 has utilized medical report platform 48 to populate the medical report (e.g., medical report 40) of patient John Smith).

When one or more specific disparate platforms (e.g., disparate platforms 46, 48, 50, 52, 54, 56) registers with the communication computing system (e.g., communication computing system 12) to receive information (e.g., data 20) concerning a specific topic (e.g., a specific patient), the one or more specific disparate platforms (e.g., disparate platforms 46, 48, 50, 52, 54, 56) may subscribe 252 with the communication computing system (e.g., communication computing system 12) to receive information (e.g., data 20) concerning the specific topic (e.g., a specific patient) that is broadcast by the communication computing system (e.g., communication computing system 12).

Accordingly, medical report platform 48 may subscribe 252 with communication computing system 12 to receive information (e.g., data 20) concerning the specific topic (e.g., patient John Smith) that is broadcast by the communication computing system (e.g., communication computing system 12). Once medical report platform 48 is subscribed 252, any information that concerns the specific topic for which medical report platform 48 has subscribed (in this example, patient John Smith) will be broadcast to medical report platform 48. Accordingly, any and all information that concerns patient John Smith (such as chest x-ray image 160) will be broadcast to/received by medical report platform 48. Conversely, any and all information that concerns other patients (for which medical report platform 48 has not subscribed) will not be broadcast to/received by medical report platform 48.

For the following example, assume that medical report platform 48 subscribed 252 to receive information concerning patient John Smith. Further assume that medical image platform 46 provides another x-ray image (e.g., data 62) that concerns patient John Smith. As discussed above, communication computing system 12 (in combination with communication process 10) may be configured to effectuate communication between computing systems 30, 32, 34, 36, wherein communication computing system 12 may receive data from one disparate platform and broadcast the data to another disparate platform. Accordingly, communication process 10 may receive 254, on the communication computing system (e.g., communication computing system 12), information (e.g., data 62) concerning the specific topic (e.g., patient John Smith).

When receiving 254, on the communication computing system (e.g., communication computing system 12), information (e.g., data 62) concerning the specific topic, communication process 10 may receive 256 on communication computing system 12 information concerning various topics. As could be imagined, since communication computing system 12 effectuates communication between computing systems 30, 32, 34, 36, communication computing system 12 would receive information concerning various topics (e.g., various patients in this example).

Further and when receiving 254, on the communication computing system (e.g., communication computing system 12), information (e.g., data 62) concerning the specific topic (e.g., a specific patient), communication process 10 may process 258 the information concerning the various topics (e.g., various patients) to determine if the information concerning the various topics (e.g., various patients) includes information (e.g., data 62) concerning the specific topic (e.g., patient John Smith).

Communication process 10 may provide 260 the information (e.g., data 62) concerning the specific topic (e.g., patient John Smith) to the one or more specific disparate platforms (e.g., medical report platform 48) that registered with the communication computing system (e.g., communication computing system 12) to receive information (e.g., data 62) concerning the specific topic (e.g., patient John Smith).

When providing 260 the information (e.g., data 62) concerning the specific topic (e.g., patient John Smith) to the one or more specific disparate platforms (e.g., medical report platform 48) that registered with the communication computing system (e.g., communication computing system 12) to receive information (e.g., data 62) concerning the specific topic (e.g., patient John Smith), communication process 10 may proactively broadcast 262 the information (e.g., data 62) concerning the specific topic (e.g., patient John Smith) to the one or more specific disparate platforms (e.g., medical report platform 48) that registered with the communication computing system (e.g., communication computing system 12) to receive information (e.g., data 62) concerning the specific topic (e.g., patient John Smith).

Accordingly and in this example, medical report platform 48 receives all information that concerns patient John Smith and does not receive information that concerns other patients for which they did not register.

D) Exposing an Endpoint

Figure 6:
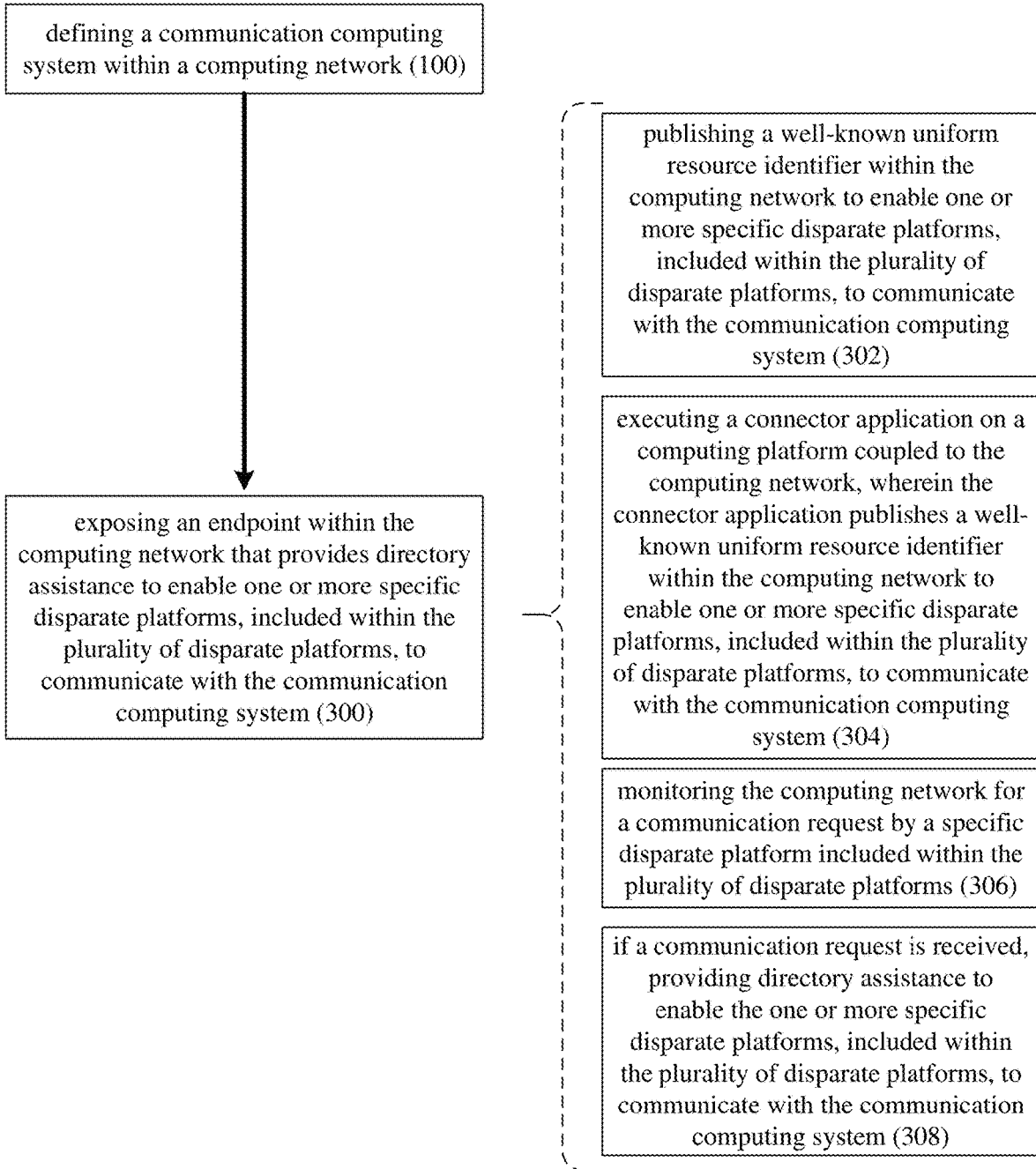
FIG. 6 is a flow chart of another implementation of the communication process of FIG. 1 according to an implementation of this disclosure.

Referring also to FIG. 6 and as discussed above, communication process 10 may define 100 a communication computing system (e.g., communication computing system 12) within a computing network (e.g., network 14 and/or network 18). This computing network (e.g., network 14 and/or network 18) may couple various computing systems (e.g., computing systems 12, 30, 32, 34, 36) configured to provide information (e.g., data 20) concerning various topics. Disparate platforms (e.g., disparate platforms 46, 48, 50, 52, 54, 56) executed on these computing systems (e.g., computing systems 12, 30, 32, 34, 36) may generate and/or modify information (e.g., data 20), which may be provided to other computing systems within the computing network (e.g., network 14 and/or network 18).

Further and as discussed above, communication computing system 12 (in combination with communication process 10) may be configured to effectuate communication between computing systems 30, 32, 34, 36, wherein communication computing system 12 may receive data from one disparate platform and broadcast the data to another disparate platform.

Further and as discussed above, communication computing system 12 may be a local computing system directly coupled to e.g., computing systems 30, 32, 34, 36 via a local area network (e.g., network 14) and/or a cloud-based computing system (e.g., a cloud-based resource) indirectly coupled to e.g., computing systems 30, 32, 34, 36 via network 18 (e.g., the internet). Accordingly and in order for such communication to occur, the location of communication computing system 12 must be known to the disparate platforms (e.g., disparate platforms 46, 48, 50, 52, 54, 56)

In order to effectuate such communication, communication process 10 may expose 300 an endpoint (e.g., endpoint 64) within the computing network (e.g., network 14 and/or network 18) that provides directory assistance to enable one or more specific disparate platforms, included within the plurality of disparate platforms (e.g., disparate platforms 46, 48, 50, 52, 54, 56), to communicate with the communication computing system (e.g., communication computing system 12).

As used in this disclosure and as will be discussed below in greater detail, an endpoint (e.g., endpoint 64) may be any feature/functionality that provides directory assistance to enable the disparate platforms (e.g., disparate platforms 46, 48, 50, 52, 54, 56) to ascertain the location of communication computing system 12.

For example and when exposing 300 an endpoint (e.g., endpoint 64) within the computing network (e.g., network 14 and/or network 18), communication process 10 may publish 302 a well-known uniform resource identifier (e.g., URI 66) within the computing network (e.g., network 14 and/or network 18) to enable one or more specific disparate platforms, included within the plurality of disparate platforms (e.g., disparate platforms 46, 48, 50, 52, 54, 56), to communicate with the communication computing system (e.g., communication computing system 12).

As is known in the art, a uniform resource identifier (e.g., URI 66) is a unique identifier used by web technologies. URIs may be used to identify anything, including real-world objects (e.g., people and places, concepts, or information resources such web pages and books). Some URIs provide a means of locating and retrieving information resources on a network (e.g., either on the Internet or on another private network, such as a computer filesystem or an Intranet), wherein these are referred to as Uniform Resource Locators (URLs). Other URIs may provide only a unique name, without a means of locating or retrieving the resource or information about it, wherein these are referred to as Uniform Resource Names (URNs).

Further and when exposing 300 an endpoint (e.g., endpoint 62) within the computing network (e.g., network 14 and/or network 18), communication process 10 may execute 304 a connector application (e.g., connector application 68)

on a computing platform (e.g., workstation computing system 68) coupled to the computing network (e.g., network 14 and/or network 18), wherein the connector application (e.g., connector application 68) publishes the well-known uniform resource identifier (e.g., URI 66) within the computing network (e.g., network 14 and/or network 18) to enable one or more specific disparate platforms, included within the plurality of disparate platforms (e.g., disparate platforms 46, 48, 50, 52, 54, 56), to communicate with the communication computing system (e.g., communication computing system 12)

When exposing 300 an endpoint (e.g., endpoint 62) within the computing network (e.g., network 14 and/or network 18), communication process 10 may monitor 306 the computing network (e.g., network 14 and/or network 18) for a communication request (e.g., request 70) by a specific disparate platform included within the plurality of disparate platforms (e.g., disparate platforms 46, 48, 50, 52, 54, 56).

Further and when exposing 300 an endpoint (e.g., endpoint 62) within the computing network (e.g., network 14 and/or network 18), communication process 10 may provide 308 directory assistance (if a communication request (e.g., request 70) is received) to enable the one or more specific disparate platforms, included within the plurality of disparate platforms (e.g., computing systems 12, 28, 30, 32, 34), to communicate with the communication computing system (e.g., communication computing system 12).

For the following example, assume that communication computing system 12 is a cloud-based resource and, therefore, is not directly coupled to network 14 but is indirectly coupled to network 14 through network 18 (e.g., the internet). Accordingly, URI 66 may identify the internet-based location of cloud-based communication computing system 12.

For example, upon workstation computing system 36 starting up and/or initiating a session, communication process 10 may expose 300 endpoint 64 within the computing network (e.g., network 14 and/or network 18), wherein endpoint 64 may be configured to provide directory assistance that enables one or more disparate platforms (included within disparate platforms 46, 48, 50, 52, 54, 56) to communicate with communication computing system 12. Specifically and when exposing 300 endpoint 62 within the computing network (e.g., network 14 and/or network 18), communication process 10 may execute 304 connector application 68 on workstation computing system 68, wherein connector application 68 publishes URI 66 so that any disparate platforms (included within disparate platforms 46, 48, 50, 52, 54, 56) may communicate with communication computing system 12.

For the various reason discussed above, medical report platform 48 may be interested in receiving all information that concerns patient John Smith (as clinician 38 has utilized medical report platform 48 to populate the medical report (e.g., medical report 40) of patient John Smith. Therefore, medical report platform 48 may wish to subscribe to receive information (e.g., data 20) concerning patient John Smith from communication computing system 12. Accordingly, medical report platform 48 may generate and provide a communication request (e., request 70) for communication with communication computing system 12.

As discussed above, communication process 10 may monitor 306 the computing network (e.g., network 14 and/or network 18) for a communication request (e.g., request 70) by (in this example) medical report platform 48. Upon receiving request 70, communication process 10 may provide 308 directory assistance to enable (in this example) medical report platform 48 to communicate with communication computing system 12. Specifically, communication process 10 may provide 308 directory assistance by e.g., having connector application 68 publishes URI 66 so that medical report platform 48 knows the location (i.e., address) of communication computing system 12.

E) Populating Medical Reports

Figure 7:
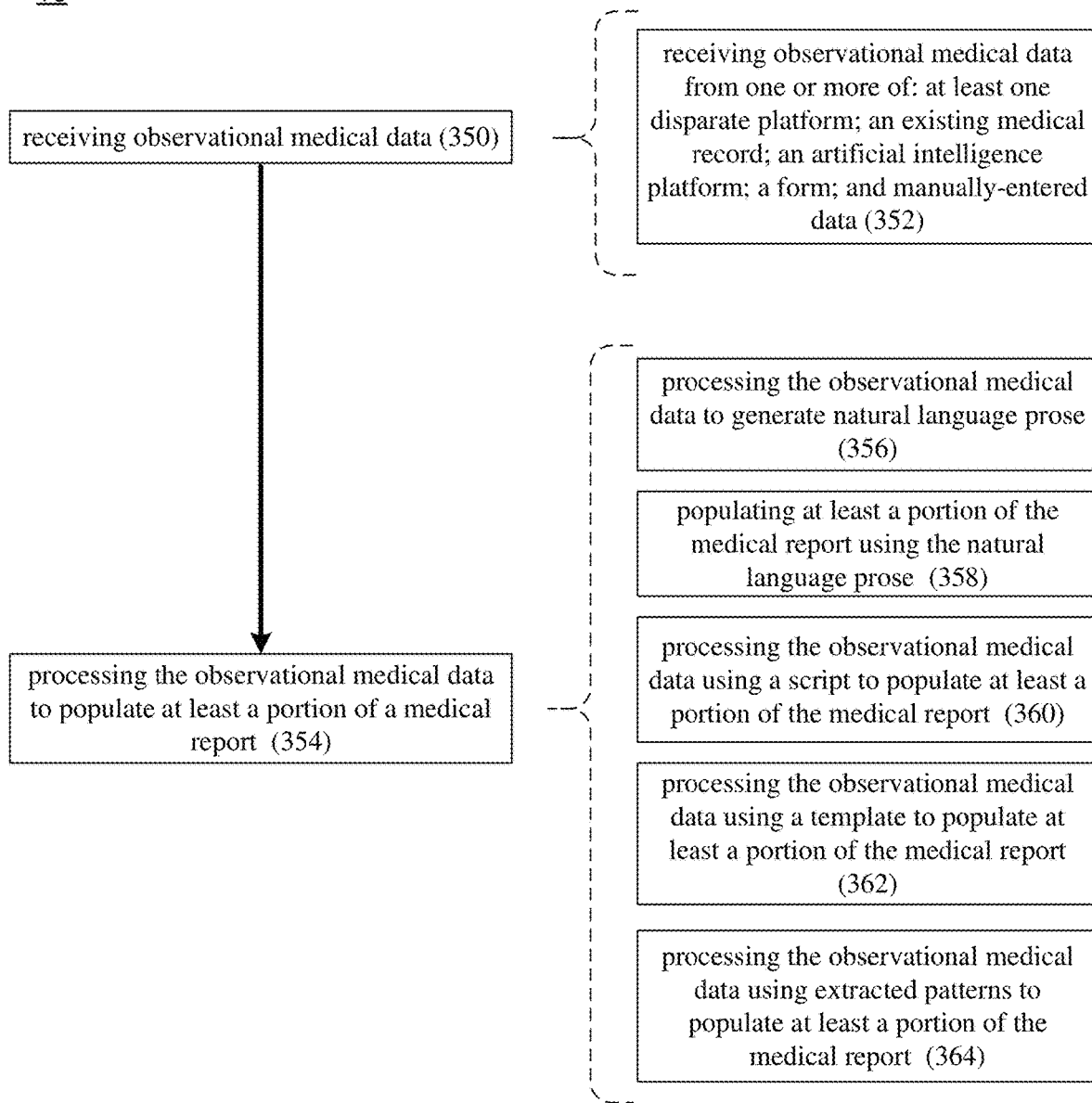
FIG. 7 is a flow chart of another implementation of the communication process of FIG. 1 according to an implementation of this disclosure.

Referring also to FIG. 7, communication process 10 may receive 350 observational medical data (e.g., data 58). When receiving 350 this observational medical data (e.g., data 58), communication process 10 may receive 352 observational medical data (e.g., data 58) from one or more of:

At Least One Disparate Platform: For example, communication process 10 may be configured to obtain observational medical data (e.g., data 58) from any of the disparate platform (e.g., disparate platforms 46, 48, 50, 52, 54, 56) that are accessible to communication process 10.

An Existing Medical Record: For example, communication process 10 may be configured to process existing medical records (e.g., medical records 72) available via medical record platform 50 to extract observational medical data (e.g., data 58).

An Existing Medical Report: For example, communication process 10 may be configured to process existing medical reports (e.g., medical reports 74) available via medical report platform 48 to extract observational medical data (e.g., data 58).

An Artificial Intelligence Platform: For example, communication process 10 may be configured to utilize an artificial intelligence platform (e.g., medical analysis platform 56) to process (for example) existing medical records (e.g., medical records 72), existing medical reports (e.g., medical reports 74), existing medical forms (e.g., handwritten note 76) and existing medical recordings (e.g., voice recording 78) to extract observational medical data (e.g., data 58).

Manually-Entered Data: For example, communication process 10 may be configured to receive observational medical data (e.g., data 58) manually entered by clinician 38 via e.g., audio input device 42, a keyboard (not shown) and/or a pointing device (not shown) coupled to workstation computing system 36.

Accordingly and when utilizing observational medical data (e.g., data 58) to populate a medical report (e.g., medical report 40), this observational medical data (e.g., data 58) may be obtained from basically any source. Further and as will be discussed below in greater detail, this observational data (e.g., data 58) need not be provided by a human being (e.g., clinician 38) and may be provided without human intervention via e.g., artificial intelligence.

Once received 350, communication process 10 may process 354 the observational medical data (e.g., data 58) to populate at least a portion of a medical report (e.g., medical report 40).

When processing 354 the observational medical data (e.g., data 58) to populate at least a portion of a medical report (e.g., medical report 40), communication process 10 may:

process 356 the observational medical data (e.g., data 58) to generate natural language prose 80 using e.g., conversational AI platform 52; and populate 358 at least a portion of the medical report (e.g., medical report 40) using natural language prose 80.

Continuing with the above-stated example, the observational data (e.g., data 58) for patient John Smith identifies the following:

PATIENT: John Smith;
TYPE: Growth;
LOCATION: Lower Quadrant of Left Lung; and
SIZE: 5.1 Centimeters.

Accordingly and upon receiving 350 observational medical data 58 (e.g., John Smith, Growth, Lower Quadrant of Left Lung, 5.1 Centimeters), communication process 10 may process 356 the observational medical data (e.g., data 58) to generate natural language prose 80 using e.g., conversational AI platform 52 executed on report computing system 34. For example, communication process 10 may process 356 observational medical data 58 (e.g., John Smith, Growth, Lower Quadrant of Left Lung, 5.1 Centimeters) to generate natural language prose 80, an example of which may include but is not limited to "Patient John Smith has a growth in the lower quadrant of left lung that measures 5.1 centimeters". Once natural language prose 80 is generated, communication process 10 may populate 358 at least a portion of the medical report (e.g., medical report 40) using natural language prose 80. For example, communication process 10 may populate 358 field 164 within medical report 40 to state that "Patient John Smith has a growth in the lower quadrant of left lung that measures 5.1 centimeters"

Additionally/alternatively and when processing 354 the observational medical data (e.g., data 58) to populate at least a portion of a medical report (e.g., medical report 40), communication process 10 may process 360 the observational medical data (e.g., data 58) using a script (e.g., script 82) to populate at least a portion of the medical report (e.g., medical report 40). For example, script 82 may be defined by e.g., clinician 38 and may generally function as an if/then statement that may be used when mapping data into the appropriate fields within medical report 40. For example, script 82 may define keywords and/or standardized medical codes that are associable with specific fields within a medical report. For example, the keyword:

"renal" may be associable with the "Kidneys" field within medical report 40;

"pneumonia" may be associable with the "Lungs" field within medical report 40; and "aorta" may be associable with the "Heart" field within medical report 40.

Additionally, script 82 may be utilized to quantify an entity. For example, script 82 say that:

if a growth 6.00 cm or greater, it is a large growth;
if a growth is 3.00-5.99 cm, it is a medium growth; and
if a growth is less than 2.99 cm, it is a small growth.

Additionally/alternatively and when processing 354 the observational medical data (e.g., data 58) to populate at least a portion of a medical report (e.g., medical report 40), communication process 10 may process 362 the observational medical data (e.g., data 58) using a template (e.g., template 84) to populate at least a portion of the medical report (e.g., medical report 40). For example, template 84 may be manually-defined by e.g., clinician 38 and may generally provide the structure for the language that is used to populate medical report 40.

In the example discussed above, communication process 10 may populate process medical report 40 with "Patient John Smith has a growth in the lower quadrant of left lung that measures 5.1 centimeters". As discussed above, the observational data (e.g., data 58) included within this statement is "_____ John Smith _____ growth _____ lower quadrant of left lung _____ 5.1 centimeters". Accordingly, an example of template 84 (which may define the structure for this statement) may be "Patient _____ has a _____ in the _____ that measures _____".

While template 84 is described above as being defined by a human being (e.g., clinician 38), other configurations are possible and are considered to be within the scope of this disclosure. For example and as will be discussed below in greater detail, template 84 may be generated via artificial intelligence.

Accordingly and when processing 354 the observational medical data (e.g., data 58) to populate at least a portion of a medical report (e.g., medical report 40), communication process 10 may process 364 the observational medical data (e.g., data 58) using extracted patterns (e.g., extracted patterns 86) to populate at least a portion of the medical report (e.g., medical report 40), wherein these extracted patterns (e.g., extracted patterns 86) may be used to generate one or more templates (e.g., template 84).

For example, these extracted patterns (e.g., extracted patterns 86) may be generated using artificial intelligence (via e.g., medical analysis platform 56) to process a plurality of previously-generated medical reports (e.g., medical reports 74). For example, communication process 10 may utilize medical analysis platform 56 to analyze medical reports 74 to identify patterns within these medical reports.

As is known in the art, pattern recognition is the process of recognizing patterns using a machine learning algorithm. Pattern recognition may be defined as the classification of data based on knowledge already gained or on statistical information extracted from patterns and/or their representation. Pattern recognition is generally the ability to detect arrangements of characteristics or data that yield information about a given system or data set. In a technological context, a recognized patterns might be recurring sequences of data over time that may be used to predict trends, particular configurations of features in images that identify objects, frequent combinations of words and phrases for natural language processing (NLP), or particular clusters of behaviors on a network that could indicate an attack.

Accordingly, communication process 10 may utilize medical analysis platform 56 to analyze previously-generated medical reports 74 to identify patterns (e.g., extracted patterns 86) within these previously-generated medical reports 74, wherein these extracted patterns (e.g., extracted patterns 86) may be used to generate one or more templates (e.g., template 84). For example and upon communication process 10 utilizing medical analysis platform 56 to analyze previously-generated medical reports 74, an extracted pattern (e.g., extracted pattern 86) may be identified, wherein entities are typically reported as follows: "Patient _____ has a _____ in the _____ that measures _____". Accordingly, this extracted pattern may be utilized to generate one or more templates (e.g., template 84).

As will be discussed below in greater detail, these extracted patterns (e.g., extracted patterns 86) may be used by communication process 10 to define options for clinician 38 (e.g., a radiologist, a cardiologist or a pathologist) as to e.g., which field within medical report 40 a particular statement (e.g., "Patient John Smith has a growth in the lower quadrant of left lung that measures 5.1 centimeters") should be placed.

F) Medical Report Field Association

Figure 8:
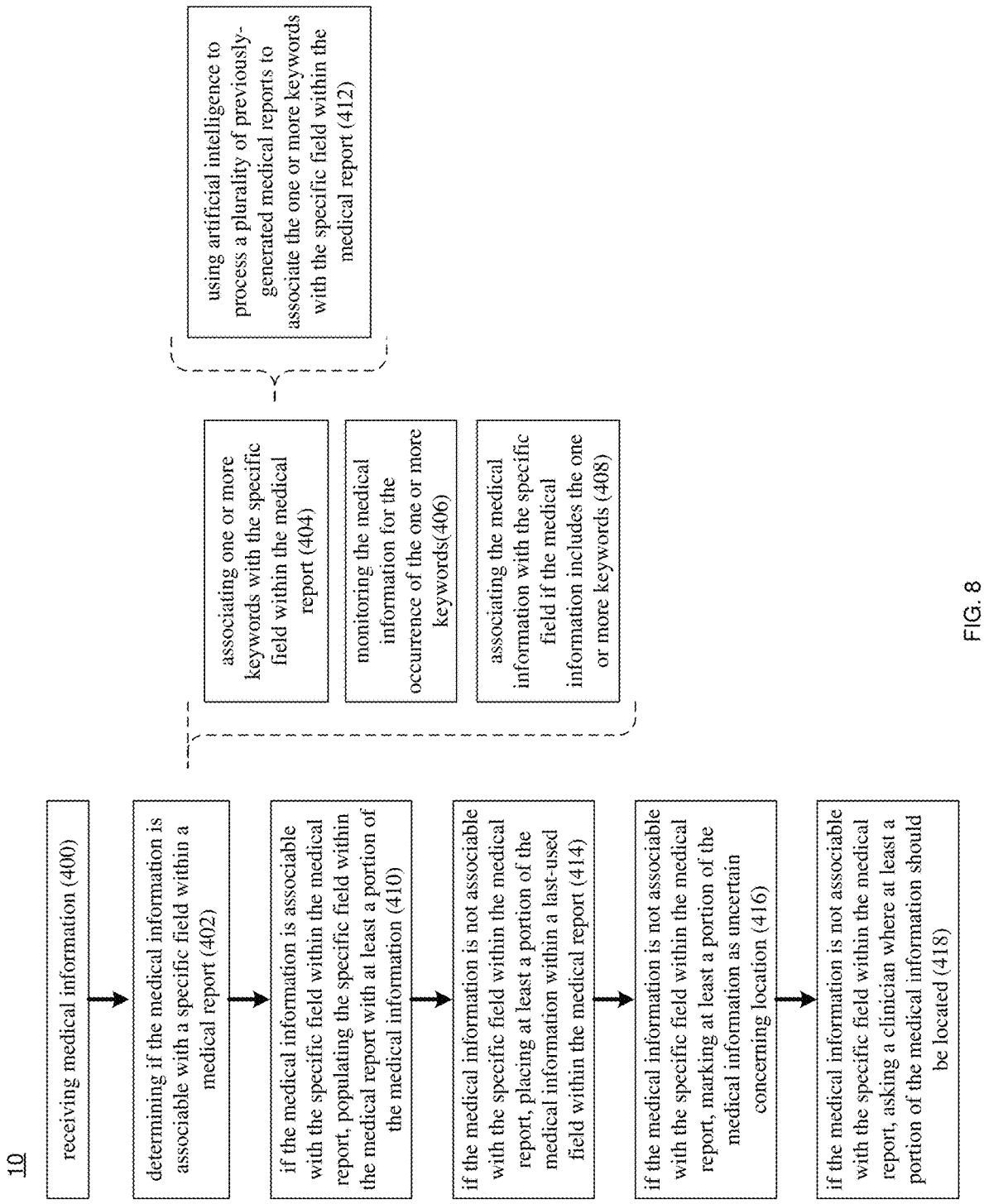
FIG. 8 is a flow chart of another implementation of the communication process of FIG. 1 according to an implementation of this disclosure.

Referring also to FIG. 8 and as discussed above, communication process 10 may receive 400 medical information (e.g., data 20). As also discussed above, communication process 10 may utilize this medical information (e.g., data 20) to populate medical reports (e.g., medical report 40).

The medical information (e.g., data 20) may include one or more of:

medical information (e.g., data 20) dictated by clinician 38 (e.g., a radiologist, a cardiologist or a pathologist). For example, clinician 38 may dictate verbal information via e.g., audio input device 42 coupled to workstation computing system 36. This verbal information may be processed via artificial intelligence platform (e.g., conversational AI platform and/or medical analysis platform 56).

medical information (e.g., data 20) obtained from at least one disparate platform (e.g., disparate platforms 46, 48, 50, 52, 54, 56).

medical information (e.g., data 20) obtained from an existing medical record (e.g., medical records 72).

medical information (e.g., data 20) obtained from an artificial intelligence platform (e.g., medical analysis platform 56).

medical information (e.g., data 20) obtained from a form (e.g., handwritten note 76).

medical information (e.g., data 20) that is manually entered by clinician 38 via e.g., a keyboard (not shown) and/or a pointing device (not shown) coupled to workstation computing system 36.

However, in order for communication process 10 to properly utilize such medical information (e.g., data 20), communication process 10 will need to know the appropriate field into which to place medical information (e.g., data 20).

Accordingly, communication process 10 may determine 402 if the medical information (e.g., data 20) is associable with a specific field (e.g., field 164) within a medical report (e.g., medical report 40).

When determining 402 if the medical information (e.g., data 20) is associable with a specific field (e.g., field 164) within a medical report (e.g., medical report 40), communication process 10 may:

associate 404 one or more keywords and/or standardized medical codes with the specific field (e.g., field 164) within the medical report (e.g., medical report 40);

monitor 406 the medical information (e.g., data 20) for the occurrence of the one or more keywords and/or standardized medical codes; and associate 408 the medical information (e.g., data 20) with the specific field if the medical information (e.g., data 20) includes the one or more keywords and/or standardized medical codes.

As discussed above, script 82 may be defined by e.g., clinician 38 and may generally function as an if/then statement that may be used when mapping data into the appropriate fields within medical report 40. For example, script 82 may define keywords and/or standardized medical codes that are associable with specific fields within a medical report. For example, the keyword:

"renal" may be associable with the "Kidneys" field within medical report 40;

"pneumonia" may be associable with the "Lungs" field within medical report 40; and "aorta" may be associable with the "Heart" field within medical report 40.

Accordingly and when determining 402 if the medical information (e.g., data 20) is associable with a specific field (e.g., field 164) within a medical report (e.g., medical report 40), communication process 10 may monitor 406 the medical information (e.g., data 20) for the occurrence of the one or more keywords and/or standardized medical codes.

Therefore:

if the medical information (e.g., data 20) includes the keyword "renal", the medical information (e.g., data 20) may be associated 408 with the "Kidneys" field (e.g., field 168) within medical report 40;

if the medical information (e.g., data 20) includes the keyword "pneumonia", the medical information (e.g., data 20) may be associated 408 with the "Lungs" field (e.g., field 164) within medical report 40; and if the medical information (e.g., data 20) includes the keyword "aorta", the medical information (e.g., data 20) may be associated 408 with the "Heart" field (e.g., field 170) within medical report 40.

If the medical information (e.g., data 20) is associable with the specific field (e.g., one of fields 164, 168, 170) within the medical report (e.g., medical report 40), communication process 10 may populate 410 the specific field (e.g., one of fields 164, 168, 170) within the medical report (e.g., medical report 40) with at least a portion of the medical information (e.g., data 20).

When associating 404 one or more keywords and/or standardized medical codes with the specific field (e.g., one of fields 164, 168, 170) within the medical report (e.g., medical report 40), communication process 10 may use 412 artificial intelligence (e.g., medical analysis platform 56) to process a plurality of previously-generated medical reports (e.g., medical report 40) to associate the one or more keywords and/or standardized medical codes with the specific field (e.g., one of fields 164, 168, 170) within the medical report (e.g., medical report 40).

As discussed above, pattern recognition is the process of recognizing patterns using a machine learning algorithm. Accordingly, communication process 10 may utilize medical analysis platform 56 to analyze previously-generated medical reports 74 to identify patterns (e.g., extracted patterns 86) within these previously-generated medical reports 74. These extracted patterns (e.g., extracted patterns 86) may be used to identify the above-described keywords and/or standardized medical codes.

For example, communication process 10 may use 412 artificial intelligence (e.g., medical analysis platform 56) to determine that:

96.3% of the time that "renal" is mentioned, it is in the "Kidneys" field (e.g., field 168) within medical report 40;

98.9% of the time that "pneumonia" is mentioned, it is in the "Lungs" field (e.g., field 164) within medical report 40; and 97.4% of the time that "aorta" is mentioned, it is in the "Heart" field (e.g., field 170) within medical report 40.

Accordingly, communication process 10 may associate 404:

"renal" with the "Kidneys" field (e.g., field 168) within medical report 40;

"pneumonia" with the "Lungs" field (e.g., field 164) within medical report 40; and "aorta" with the "Heart" field (e.g., field 170) within medical report 40.

If the medical information (e.g., data 20) is not associable with the specific field (e.g., one of fields 164, 168, 170) within the medical report (e.g., medical report 40), communication process 10 may place 414 at least a portion of the medical information (e.g., data 20) within a last-used field within the medical report (e.g., medical report 40). For example, if clinician 38 was dictating (via e.g., audio input device 42) medical information (e.g., data 20) that included the keyword "renal", that medical information (e.g., data 20) would be placed within field 168 (for the reasons discussed above). If clinician 38 paused for a bit and then dictated "So I recommend the appropriate treatment", this medical information (e.g., data 20) does not include any keywords and/or standardized medical codes. However, being it was dictated following information that was associable with field 168, communication process 10 may place 414 at least a portion of the medical information (e.g., "So I recommend the appropriate treatment") within a last-used field (e.g., field 168) within the medical report (e.g., medical report 40).

Additionally/alternatively, if the medical information (e.g., data 20) is not associable with the specific field (e.g., one of fields 164, 168, 170) within the medical report (e.g., medical report 40), communication process 10 may mark 416 at least a portion of the medical information (e.g., data 20) as uncertain concerning location. For example, communication process 10 may insert a parenthetical (e.g., PLEASE CONFIRM LOCATION) prior to or after the information in question to mark 416 the location of the information as uncertain.

Further and if the medical information (e.g., data 20) is not associable with the specific field (e.g., one of fields 164, 168, 170) within the medical report (e.g., medical report 40), communication process 10 may ask 418 clinician 38 (e.g., a radiologist, a cardiologist or a pathologist) where at least a portion of the medical information (e.g., data 20) should be located. For example, communication process 10 may render popup window 172 that asks 418 clinician 38 to confirm the location of the information in question.

G) Identifying Actionable Items

Figure 9:
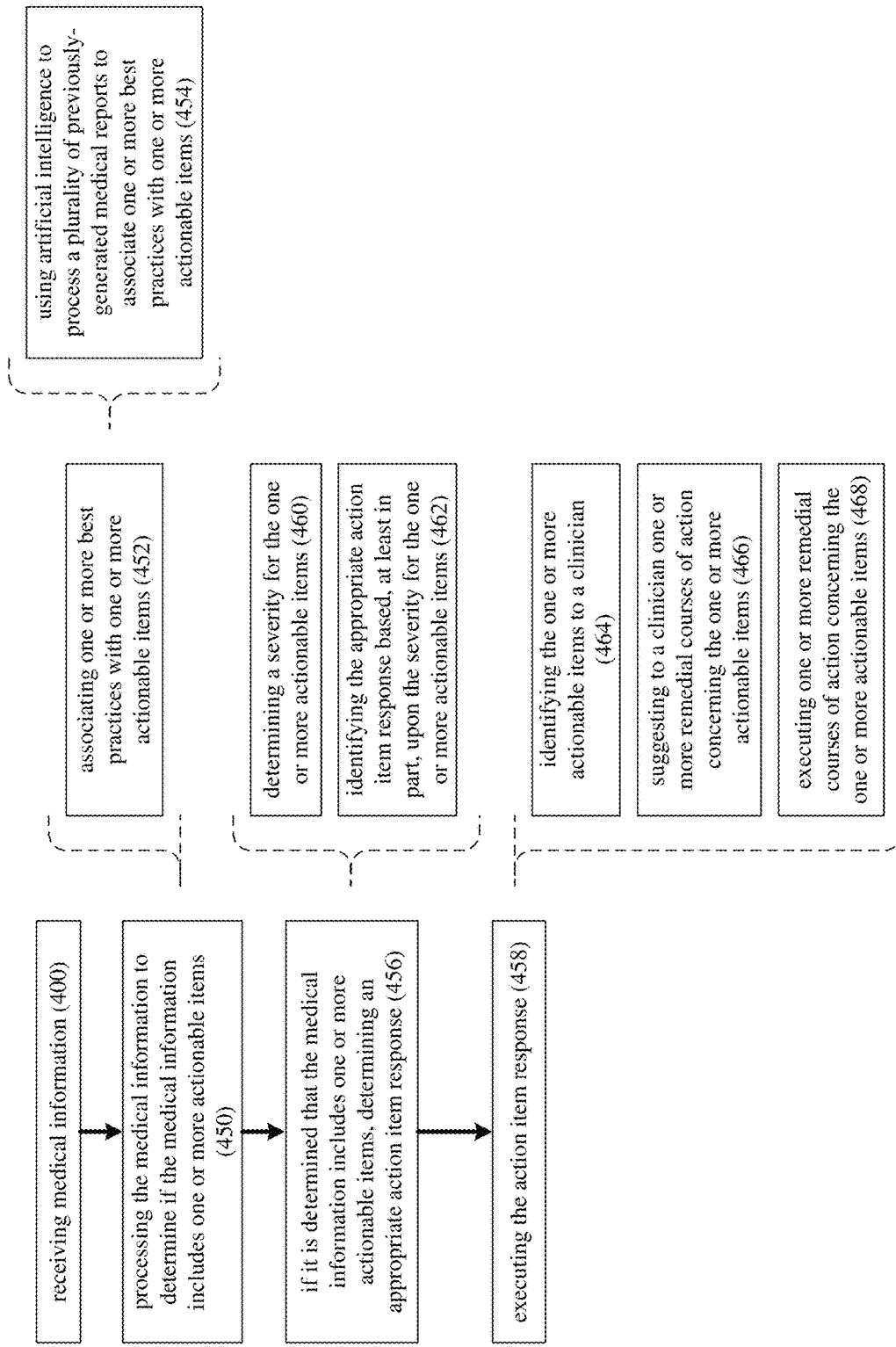
FIG. 9 is a flow chart of another implementation of the communication process of FIG. 1 according to an implementation of this disclosure.

Referring also to FIG. 9 and as discussed above, communication process 10 may receive 400 medical information (e.g., data 20). As also discussed above, communication process 10 may utilize this medical information (e.g., data 20) to populate medical reports (e.g., medical report 40)

As discussed above, this medical information (e.g., data 20) may include one or more of:

- medical information (e.g., data 20) dictated by clinician 38 (e.g., a radiologist, a cardiologist or a pathologist). For example, clinician 38 may dictate verbal information via e.g., audio input device 42 coupled to workstation computing system 36. This verbal information may be processed via artificial intelligence platform (e.g., conversational AI platform and/or medical analysis platform 56).
- medical information (e.g., data 20) obtained from at least one disparate platform (e.g., disparate platforms 46, 48, 50, 52, 54, 56).
- medical information (e.g., data 20) obtained from an existing medical record (e.g., medical records 72).
- medical information (e.g., data 20) obtained from an artificial intelligence platform (e.g., medical analysis platform 56).
- medical information (e.g., data 20) obtained from a form (e.g., handwritten note 76).
- medical information (e.g., data 20) that is manually entered by clinician 38 via e.g., a keyboard (not shown) and/or a pointing device (not shown) coupled to workstation computing system 36.

Communication process 10 may process 450 the medical information (e.g., data 20) to determine if the medical information (e.g., data 20) includes one or more actionable items. For the following discussion, an actionable item may be something included within medical information (e.g., data 20) that requires some form of follow up/intervention. As could be imagined, these actionable items (and the associated follow up) may vary in severity from low severity to high severity. For example:

- If medical information (e.g., data 20) includes a patient's weight, and the weight of the patient has increased ten pounds since the last time that the patient visited the doctor; this may be considered a low-severity actionable item.
- If medical information (e.g., data 20) includes the patient's blood pressure, and the blood pressure of the patient is 160 over 120; this may be considered a mid-severity actionable item.
- If medical information (e.g., data 20) includes an MRI image of a patient's brain, and the MRI image reveals a brain bleed situation; this may be considered a high-severity actionable item.

The actionable items that may be included within the medical information (e.g., data 20) may be defined in various mays. For example, some actionable items may be easily definable via a script (e.g., script 82).

For example and with respect to the blood pressure of a patient, script 82 may define the following:

|  | Systolic (mm Hg) | Diastolic (mm Hg) |
|---|---|---|
| Normal | Below 120 | Below 80 |
| Elevated (hypertension) | 120-129 | Below 80 |
| Stage 1 hypertension | 130-139 | 80-90 |
| Stage 2 hypertension | 140 or above | 90 or above |
| Hypertensive crisis | Over 180 | Over 120 |

Further and with respect to the weight of a patient, script 82 may define the following:

| | BMI | | | | | | | | | | | | | | | | | |
|---|---|---|---|---|---|---|---|---|---|---|---|---|---|---|---|---|---|---|
| Height (inches) | 19 | 20 | 21 | 22 | 23 | 24 | 25 | 26 | 27 | 28 | 29 | 30 | 31 | 32 | 33 | 34 | 35 |
| | | | | | | | Body Weight (pounds) | | | | | | | | | | | |
| 58 | 91 | 96 | 100 | 105 | 110 | 115 | 119 | 124 | 129 | 134 | 138 | 143 | 148 | 153 | 158 | 162 | 167 |
| 59 | 94 | 99 | 104 | 109 | 114 | 119 | 124 | 128 | 133 | 138 | 143 | 148 | 153 | 158 | 163 | 168 | 173 |
| 60 | 97 | 102 | 107 | 112 | 118 | 123 | 128 | 133 | 138 | 143 | 148 | 153 | 158 | 163 | 168 | 174 | 179 |
| 61 | 100 | 106 | 111 | 116 | 122 | 127 | 132 | 137 | 143 | 148 | 153 | 158 | 164 | 169 | 174 | 180 | 185 |
| 62 | 104 | 109 | 115 | 120 | 126 | 131 | 136 | 142 | 147 | 153 | 158 | 164 | 169 | 175 | 180 | 186 | 191 |
| 63 | 107 | 113 | 118 | 124 | 130 | 135 | 141 | 146 | 152 | 158 | 163 | 169 | 175 | 180 | 186 | 191 | 197 |
| 64 | 110 | 116 | 122 | 128 | 134 | 140 | 145 | 151 | 157 | 163 | 169 | 174 | 180 | 186 | 192 | 197 | 204 |
| 65 | 114 | 120 | 126 | 132 | 138 | 144 | 150 | 156 | 162 | 168 | 174 | 180 | 186 | 192 | 198 | 204 | 210 |
| 66 | 118 | 124 | 130 | 136 | 142 | 148 | 155 | 161 | 167 | 173 | 179 | 186 | 192 | 198 | 204 | 210 | 216 |
| 67 | 121 | 127 | 134 | 140 | 146 | 153 | 159 | 166 | 172 | 178 | 185 | 191 | 198 | 204 | 211 | 217 | 223 |
| 68 | 125 | 131 | 138 | 144 | 151 | 158 | 164 | 171 | 177 | 184 | 190 | 197 | 203 | 210 | 216 | 223 | 230 |
| 69 | 128 | 135 | 142 | 149 | 155 | 162 | 169 | 176 | 182 | 189 | 196 | 203 | 209 | 216 | 223 | 230 | 236 |
| 70 | 132 | 139 | 146 | 153 | 160 | 167 | 174 | 181 | 188 | 195 | 202 | 209 | 216 | 222 | 229 | 236 | 243 |
| 71 | 136 | 143 | 150 | 157 | 165 | 172 | 179 | 186 | 193 | 200 | 208 | 215 | 222 | 229 | 236 | 243 | 250 |
| 72 | 140 | 147 | 154 | 162 | 169 | 177 | 184 | 191 | 199 | 206 | 213 | 221 | 228 | 235 | 242 | 250 | 258 |

-continued

| | BMI | | | | | | | | | | | | | | | | |
|---|---|---|---|---|---|---|---|---|---|---|---|---|---|---|---|---|---|
| Height (inches) | 19 | 20 | 21 | 22 | 23 | 24 | 25 | 26 | 27 | 28 | 29 | 30 | 31 | 32 | 33 | 34 | 35 |
| | | | | | | | Body Weight (pounds) | | | | | | | | | | |
| 73 | 144 | 151 | 159 | 166 | 174 | 182 | 189 | 197 | 204 | 212 | 219 | 227 | 235 | 242 | 250 | 257 | 265 |
| 74 | 148 | 155 | 163 | 171 | 179 | 186 | 194 | 202 | 210 | 218 | 225 | 233 | 241 | 249 | 256 | 264 | 272 |
| 75 | 152 | 160 | 168 | 176 | 184 | 192 | 200 | 208 | 216 | 224 | 232 | 240 | 248 | 256 | 264 | 272 | 279 |
| 76 | 156 | 164 | 172 | 180 | 189 | 197 | 205 | 213 | 221 | 230 | 238 | 246 | 254 | 263 | 271 | 279 | 287 |

Accordingly and for such numerically-quantifiable actionable items, script 82 may be configured to define such action items, as well as associate a severity with the action item that depends upon e.g., the actionable item's position within the above-referenced tables.

However, some actionable items may not be based upon numbers. For example, a brain bleed is not based upon numbers and is based upon what appears within an image of a patient's brain. Additionally, a growth in the lung of a patient is not based upon numbers and is based upon what appears in an image of a patient's chest.

As discussed above, pattern recognition is the process of recognizing patterns using a machine learning algorithm. Accordingly, communication process 10 may utilize medical analysis platform 56 to analyze e.g., medical records 72, previously-generated medical reports 74, and/or medical images (e.g., chest x-ray image 160 available from medical image platform 46) to identify patterns (e.g., extracted patterns 86) within these medical records 72, previously-generated medical reports 74, and/or medical images (e.g., chest x-ray image 160 available from medical image platform 46).

For example, medical images in combination with medical reports/records may be analyzed to determine:
what a typical brain bleed looks like;
what a typical aortic aneurysm looks like, and
what a typical lung tumor looks like.

These extracted patterns (e.g., extracted patterns 86) may be used identify the above-described actionable items.

When processing 450 the medical information (e.g., data 20) to determine if the medical information (e.g., data 20) includes one or more actionable items, communication process 10 may associate 452 one or more best practices with one or more actionable items.

Some of these best practices may be easily definable via e.g., script 82. For example, if you are ten pounds overweight, you need to eat less and/or exercise more until you lose the ten pounds. If your blood pressure is slightly elevated, you may need to exercise more. While if your blood pressure is extremely elevated, you may need to be put on high blood pressure medication.

However, some best practices may be less numerically driven and harder to discern. Accordingly and when associating 452 one or more best practices with one or more actionable items, communication process 10 may use 454 artificial intelligence (e.g., medical analysis platform 56) to process a plurality of previously-generated medical reports (e.g., previously-generated medical reports 74) to associate one or more best practices with one or more actionable items.

Again, pattern recognition is the process of recognizing patterns using a machine learning algorithm. Accordingly, communication process 10 may utilize medical analysis platform 56 to analyze e.g., medical records 72, previously-generated medical reports 74, and/or medical images (e.g., chest x-ray image 160 available from medical image platform 46) to identify patterns (e.g., extracted patterns 86) within these medical records 72, previously-generated medical reports 74, and/or medical images (e.g., chest x-ray image 160 available from medical image platform 46).

For example, medical images in combination with medical reports/records may be analyzed to determine:
what a typical response (a best practice) to a brain bleed is;
what a typical response (a best practice) to an aortic aneurysm is, and
what a typical response (a best practice) to a lung tumor is.

These extracted patterns (e.g., extracted patterns 86) may be used identify the above-described best practices.

If communication process 10 determines 450 that the medical information (e.g., data 20) includes one or more actionable items, communication process 10 may:
determine 456 an appropriate action item response; and
execute 458 the action item response.

When determining 456 an appropriate action item response, communication process 10 may:
determine 460 a severity for the one or more actionable items; and
identify 462 the appropriate action item response based, at least in part, upon the severity for the one or more actionable items.

Accordingly and as discussed above, if the blood pressure of a patient is slightly elevated, the patient may need to exercise more. However, if the blood pressure of a patient is extremely elevated, the patient may need to be put on high blood pressure medication.

When executing 458 the action item response, communication process 10 may:
identify 464 the one or more actionable items to clinician 38 (e.g., a radiologist, a cardiologist or a pathologist);
suggest 466 to clinician 38 (e.g., a radiologist, a cardiologist or a pathologist) one or more remedial courses of action concerning the one or more actionable items; and/or
execute 468 one or more remedial courses of action concerning the one or more actionable items.

For example, communication process 10 may identify 464 the one or more actionable items to clinician 38 (e.g., a radiologist, a cardiologist or a pathologist). Accordingly, clinician 38 may be informed of all actionable items (regardless of severity). Alternatively, clinician 38 may be informed of only mid-severity or high-severity actionable items. When identifying 464 the one or more actionable items to clinician 38, communication process 10 may render a popup window (e.g., popup window 172) that identifies the one or more actionable items to clinician 38.

Further, communication process 10 may suggest 466 to clinician 38 (e.g., a radiologist, a cardiologist or a pathologist) one or more remedial courses of action concerning the one or more actionable items. As discussed above, clinician 38 may be informed of some or all of the actionable items. Further, communication process 10 may make suggestions to clinician 38 concerning how to address these actionable items. When suggesting 466 one or more remedial courses of action concerning the one or more actionable items to clinician 38, communication process 10 may render a popup window (e.g., popup window 172) that suggests that clinician 38 contact oncology concerning the growth shown in chest x-ray image 160.

Additionally, communication process 10 may execute 468 one or more remedial courses of action concerning the one or more actionable items. As discussed above, clinician 38 may be informed of some or all of the actionable items and/or suggestions may be made concerning how to address some or all of the actionable items (as discussed above). Further and concerning high-severity situations, communication process 10 may automatically execute a remedial course of action. When executing 468 one or more remedial courses of action concerning the one or more actionable items, communications process 10 may e.g., automatically contact neurology and automatically schedule a surgery suite when a patient is determined to have a brain bleed.

H) Floating Window

Figure 10:
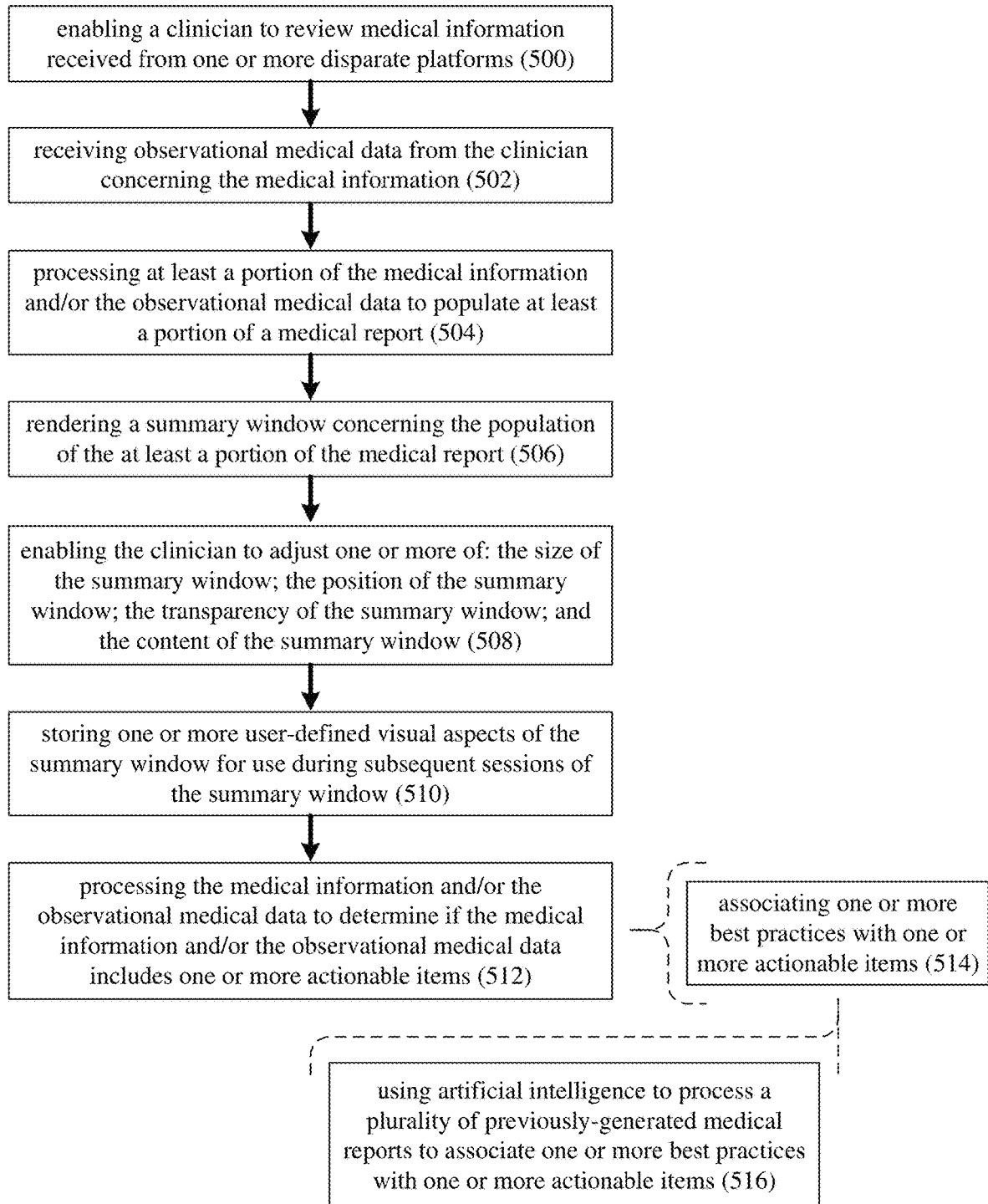
FIG. 10 is a flow chart of another implementation of the communication process of FIG. 1 according to an implementation of this disclosure.

Referring also to FIG. 10 and as discussed above, communication process 10 may enable 500 clinician 38 (e.g., a radiologist, a cardiologist or a pathologist) to review medical information (e.g., data 20) received from one or more disparate platforms (e.g., disparate platforms 46, 48, 50, 52, 54, 56). As discussed above, these disparate platforms may include disparate medical platforms (e.g., medical imaging platform 46; medical report platform 48; medical record platform 50; conversational AI platform 52; illumination platform 54 and/or medical analysis platform 56.

Further and as discussed above, communication process 10 may receive 502 observational medical data (e.g., data 58) from the clinician 38 (e.g., a radiologist, a cardiologist or a pathologist) concerning the medical information (e.g., data 20), wherein communication process 10 may process 504 at least a portion of the medical information (e.g., data 20) and/or the observational medical data (e.g., data 58) to populate at least a portion of a medical report (e.g., medical report 40).

Figure 11:
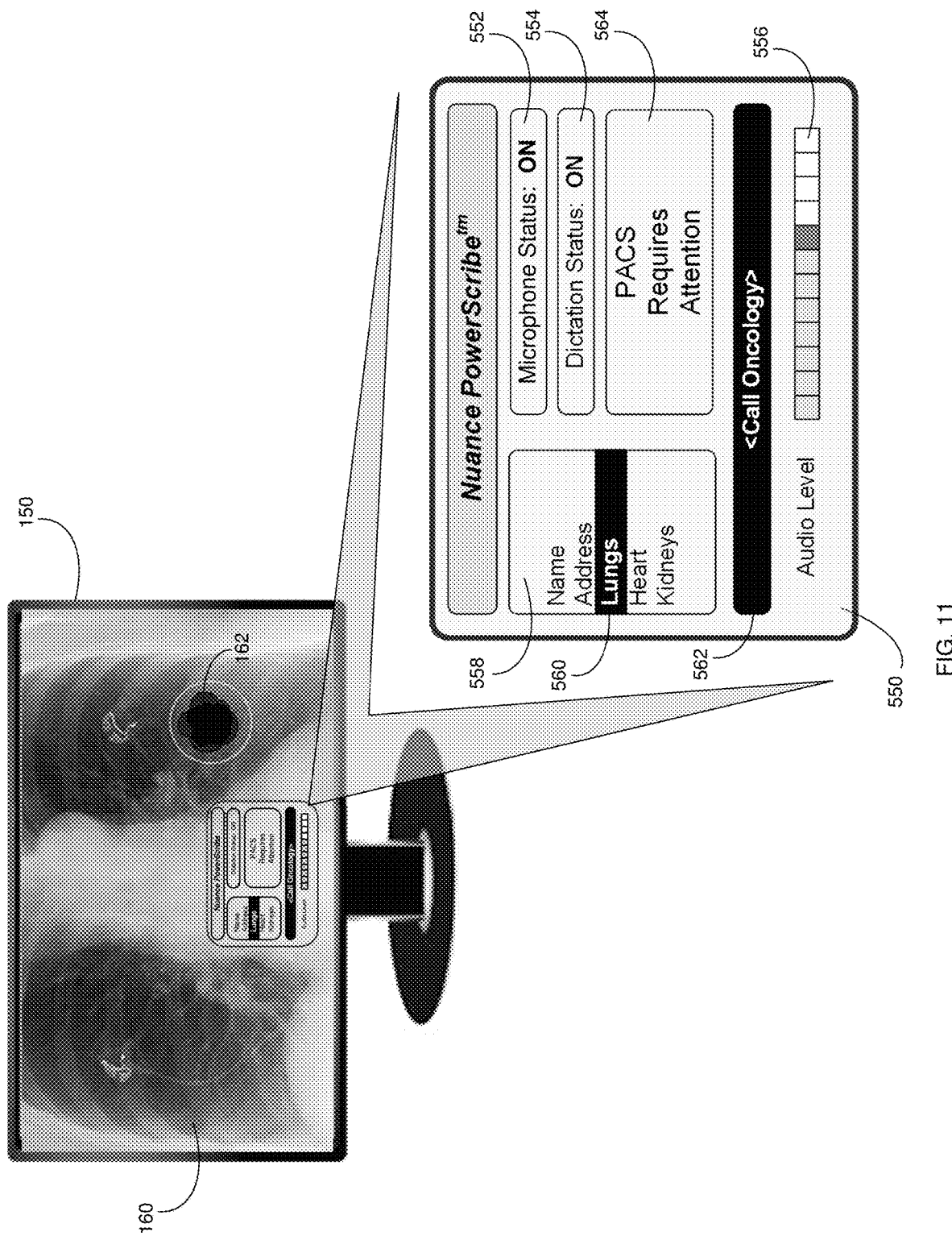
FIG. 11 is a summary window rendered by the communication process of FIG. 1.

Referring also to FIG. 11 and in order to enhance the user experience of clinician 38, communication process 10 may render 506 a summary window (e.g., summary window 550) concerning the population of the at least a portion of the medical report (e.g., medical report 40). Summary window 550 may be a transparent overlay summary window, thus allowing clinician 38 to see the information below summary window 550. Accordingly and regardless of where summary window 550 is positioned within monitor 150, the content of monitor 150 (in this example, chest x-ray image 160) will not be obscured by summary window 550.

Communication process 10 may enable 508 clinician 38 (e.g., a radiologist, a cardiologist or a pathologist) to adjust one or more of:

Summary Window Size: In a fashion similar to that of a window within a personal computer, communication process 10 may allow clinician 38 to adjust the size of summary window 550 (e.g., increased or decreased with respect to width or height).

Figure 3:
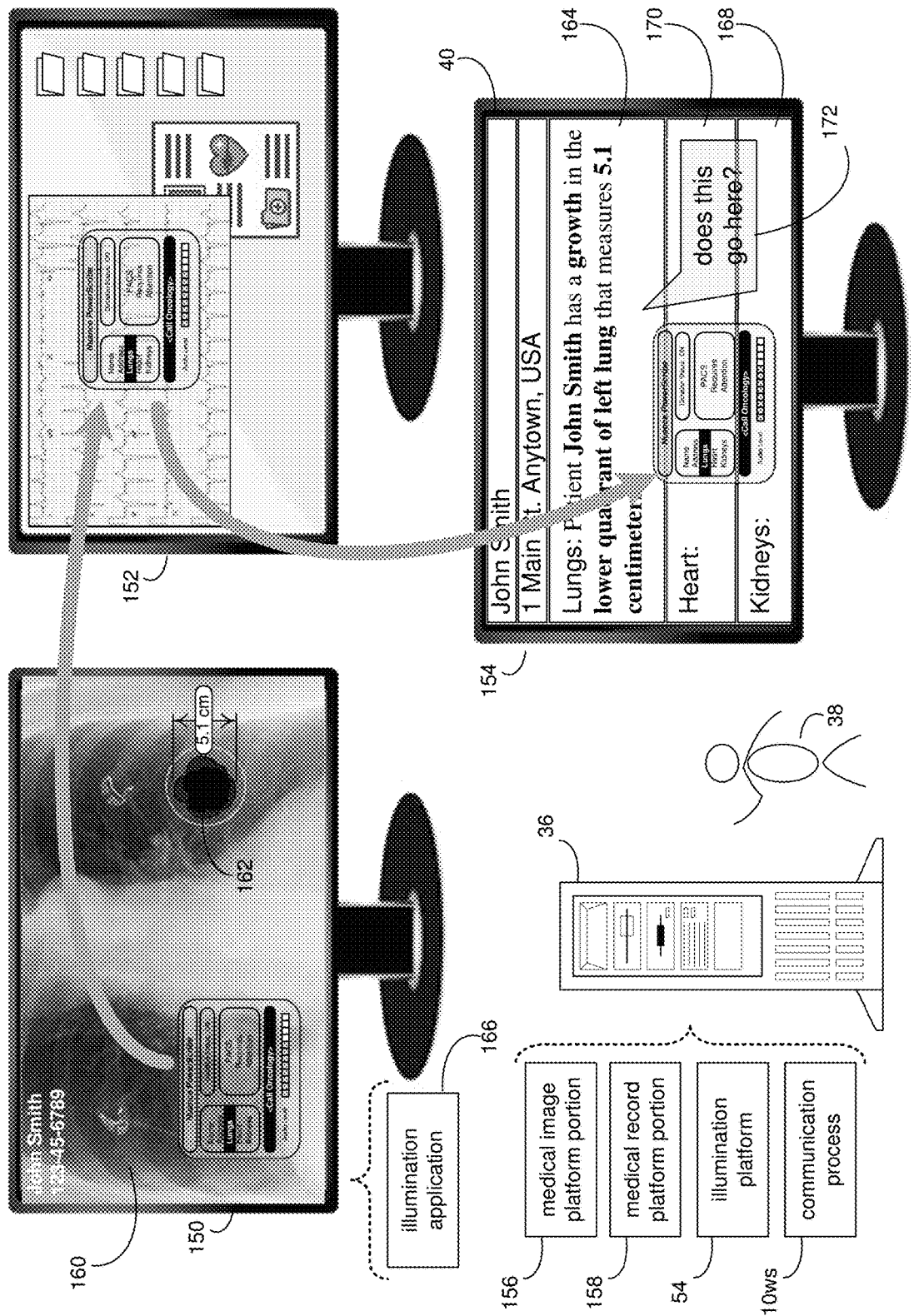
FIG. 3 is a diagrammatic view of a workstation computing system executing the communication process of FIG. 1.

Summary Window Position: In a fashion similar to that of a window within a personal computer, the position of summary window 550 may be repositioned (e.g., dragged and dropped) within the display area of monitor 150. Further and as shown in FIG. 3, summary window 550 may be repositioned amongst the various monitors (e.g., 150, 152, 154). Accordingly, communication process 10 may allow clinician 38 to position summary window 550 within the monitor on which they are currently working. So if clinician 38 is utilizing monitor 150 to review chest x-ray image 160, communication process 10 may allow clinician 38 to position summary window 550 within monitor 150 so that clinician 38 can view summary window 550 without needing to take their eyes off of (in this example) chest x-ray image 160.

Summary Window Transparency: Communication process 10 may allow clinician 38 to adjust the transparency of summary window 550, thus allowing clinician 38 to adjust how visible the content of monitor 150 is through summary window 550. For example, clinician 38 may adjust the transparency of summary window 550 from very transparent (e.g., essentially invisible) to not transparent at all (e.g., fully obscuring what is underneath summary window 550)

Summary Window Content: Communication process 10 may allow clinician 38 to adjust what is included within summary window 550. For example, communication process 10 may allow clinician 38 to decide whether summary window 550 includes:

a microphone status (e.g., microphone status indicator 552) that informs clinician 38 as to whether the microphone (e.g., audio input device 42) is currently turned on;

a current dictation mode (e.g., dictation status indicator 554) that informs clinician 38 as to whether or not they are currently in dictation mode;

an audio input level (e.g., audio input level indicator 556) that informs clinician 38 of the audio level of their voice signal (as provided by audio input device 42);

a plurality of fields (e.g., plurality of fields indicator 558) included within the medical report (e.g., medical report 40);

an active field (e.g., active field indicator 560) included within the medical report (e.g., medical report 40);

alerts (e.g., alert indicator 562) for one or more actionable items; and an application waiting (e.g., application waiting indicator 564) for input in a dialog.

Communication process 10 may store 510 one or more user-defined visual aspects (e.g., the above-described summary window size, summary window position, summary window transparency and summary windows content) of the summary window (e.g., summary window 550) for use during subsequent sessions of summary window 550. Accordingly and once clinician 38 has configured summary window 550 to their liking, these configurations may be saved so that clinician 38 does to need to reconfigure summary window 550 the next time they use the system.

Continuing with the above-described example, assume that clinician 38 is reviewing chest x-ray image 160 on monitor 150. Accordingly, clinician 38 may position summary window 550 within monitor 150 so that clinician 38 may view summary window 550 without needing to take their eyes off of chest x-ray image 160, thus providing functionality similar to that of a head-up display in a car, wherein the driver may view vital information (e.g., speed, navigation instructions, etc.) without needing to take their eyes off of the road.

As shown in FIG. 3, medical report 40 is shown to include five fields, namely patient name, patient address, lungs, heart, and kidneys. Accordingly, plurality of fields indicator 558 within summary window 550 may identify the fields included within medical report 40. While medical report 40 is shown to include only five fields, this is for illustrative purposes only and it is understood that medical report 40 may include many additional fields. Additionally, active field indicator 560 within summary window 550 may identify the field in which communication process 10 is currently entering data. As discussed above, communication process 10 may enter the prose "Patient John Smith has a growth in the lower quadrant of left lung that measures 5.1 centimeters". Accordingly, active field indicator 560 may indicate the "lungs" field (e.g., field 164) as the active field within medical report 40.

Further, audio input level indicator 556 within summary window 550 may be a sweeping audio level indicator that generally shows the volume/strength of the audio signal that clinician 38 is providing to audio input device 42, thus allowing clinician 38 to adjust the loudness of their voice and/or adjust the gain of audio input device 42 if the volume/strength of the audio signal is too strong or too weak.

As discussed above, communication process 10 may process 512 the medical information (e.g., data 20) and/or the observational medical data (e.g., data 58) to determine if the medical information (e.g., data 20) and/or the observational medical data (e.g., data 58) includes one or more actionable items, which may include associating 514 one or more best practices with one or more actionable items. And when associating 514 the one or more best practices with one or more actionable items, communication process 10 may use 516 artificial intelligence to process a plurality of previously-generated medical report (e.g., medical report 40) to associate one or more best practices with one or more actionable items.

Assuming that communication process 10 associates the best practice of contacting oncology when a patient has "a growth in the lower quadrant of left lung that measures 5.1 centimeters", summary window 550 may render the message "Call Oncology" within alert indicator 562 of summary window 550.

Further and as discussed above, medical images in combination with medical reports/records may be analyzed to determine: what a typical brain bleed looks like; what a typical aortic aneurysm looks like, and what a typical lung tumor looks like. Accordingly, communication process 10 and/or medical imaging platform 46 (e.g., PACS) may identify growth 162 by e.g., circling growth 162. Accordingly and to direct the attention of clinician 38 to medical imaging platform 46 (e.g., PACS) and the circled growth identified therein, communication process 10 may render the message "PACS Requires Attention" within application waiting indicator 564.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing system, comprising:
    defining, by a processor, a communication computing system within a computing network, wherein the computing network includes a plurality of disparate platforms configured to provide information concerning various topics;
    enabling, by the processor, a user to issue a verbal command concerning one or more of the plurality of disparate platforms;
    processing, by the processor, the verbal command to generate a platform-useable command based, at least in part, upon the verbal command; and
    providing, by the processor, the platform-useable command to at least a portion of the plurality of disparate platforms via the communication computing system includes receiving the platform-useable command on the communication computing system and broadcasting the platform-useable command to at least the portion of the plurality of disparate platforms,
    wherein in response of an event that the platform-useable command has some ambiguity, the at least the portion of the plurality of disparate platforms via the communication computing system is configured to make a verbal inquiry to the user to clarify the ambiguity.

2. The computer-implemented method of claim 1 wherein the plurality of disparate platforms includes a plurality of disparate medical platforms.

3. The computer-implemented method of claim 2 wherein the plurality of disparate medical platforms includes one or more of:
    a medical imaging platform;
    a medical report platform;
    a medical analysis platform;
    a medical record platform; and
    a conversational AI platform.

4. The computer-implemented method of claim 2 wherein the information concerning various topics includes information concerning various patients.

5. The computer-implemented method of claim 1 wherein the communication computing system includes a cloud-based communication computing system.

6. The computer-implemented method of claim 1 wherein at least a portion of the plurality of disparate platforms is executed on a single computing system.

7. The computer-implemented method of claim 1 wherein processing the verbal command to generate a platform-useable command based, at least in part, upon the verbal command includes:
    processing the verbal command via a conversational AI platform to generate the platform-useable command based, at least in part, upon the verbal command.

8. The computer-implemented method of claim 1 further comprising:
    receiving the platform-useable command on at least one of the plurality of disparate platforms; and
    processing the platform-useable command on the at least one of the plurality of disparate platforms.

9. A computer program product residing on a non-transitory computer readable medium having a plurality of instructions stored thereon which, when executed by a processor, cause the processor to perform operations comprising:
    defining a communication computing system within a computing network, wherein the computing network includes a plurality of disparate platforms configured to provide information concerning various topics;

enabling a user to issue a verbal command concerning one or more of the plurality of disparate platforms;

processing the verbal command to generate a platform-useable command based, at least in part, upon the verbal command; and providing the platform-useable command to at least a portion of the plurality of disparate platforms via the communication computing system includes receiving the platform-useable command on the communication computing system and broadcasting the platform-useable command to at least the portion of the plurality of disparate platforms, wherein in response of an event that the platform-useable command has some ambiguity, the at least the portion of the plurality of disparate platforms via the communication computing system is configured to make a verbal inquiry to the user to clarify the ambiguity.

10. The computer program product of claim 9 wherein the plurality of disparate platforms includes a plurality of disparate medical platforms.

11. The computer program product of claim 10 wherein the plurality of disparate medical platforms includes one or more of:
   a medical imaging platform;
   a medical report platform;
   a medical analysis platform;
   a medical record platform; and
   a conversational AI platform.

12. The computer program product of claim 10 wherein the information concerning various topics includes information concerning various patients.

13. The computer program product of claim 9 wherein the communication computing system includes a cloud-based communication computing system.

14. The computer program product of claim 9 wherein at least a portion of the plurality of disparate platforms is executed on a single computing system.

15. The computer program product of claim 9 wherein processing the verbal command to generate a platform-useable command based, at least in part, upon the verbal command includes:
   processing the verbal command via a conversational AI platform to generate the platform-useable command based, at least in part, upon the verbal command.

16. The computer program product of claim 9 further comprising:
   receiving the platform-useable command on at least one of the plurality of disparate platforms; and
   processing the platform-useable command on the at least one of the plurality of disparate platforms.

17. A computing system including a processor and memory configured to perform operations comprising:
   defining, by the processor, a communication computing system within a computing network, wherein the computing network includes a plurality of disparate platforms configured to provide information concerning various topics;

enabling, by the processor, a user to issue a verbal command concerning one or more of the plurality of disparate platforms;

processing, by the processor, the verbal command to generate a platform-useable command based, at least in part, upon the verbal command; and providing, by the processor, the platform-useable command to at least a portion of the plurality of disparate platforms via the communication computing system includes receiving the platform-useable command on the communication computing system and broadcasting the platform-useable command to at least the portion of the plurality of disparate platforms, wherein in response of an event that the platform-useable command has some ambiguity, the at least the portion of the plurality of disparate platforms via the communication computing system is configured to make a verbal inquiry to the user to clarify the ambiguity.

18. The computing system of claim 17 wherein the plurality of disparate platforms includes a plurality of disparate medical platforms.

19. The computing system of claim 18 wherein the plurality of disparate medical platforms includes one or more of:
   a medical imaging platform;
   a medical report platform;
   a medical analysis platform;
   a medical record platform; and
   a conversational AI platform.

20. The computing system of claim 18 wherein the information concerning various topics includes information concerning various patients.

21. The computing system of claim 17 wherein the communication computing system includes a cloud-based communication computing system.

22. The computing system of claim 17 wherein at least a portion of the plurality of disparate platforms is executed on a single computing system.

23. The computing system of claim 17 wherein processing the verbal command to generate a platform-useable command based, at least in part, upon the verbal command includes:
   processing the verbal command via a conversational AI platform to generate the platform-useable command based, at least in part, upon the verbal command.

24. The computing system of claim 17 further comprising:
   receiving the platform-useable command on at least one of the plurality of disparate platforms; and
   processing the platform-useable command on the at least one of the plurality of disparate platforms.

* * * * *